US010646665B2

(12) United States Patent
Haddad et al.

(10) Patent No.: US 10,646,665 B2
(45) Date of Patent: May 12, 2020

(54) SYSTEM FOR DETECTING AND REMOVING A GAS BUBBLE FROM A VASCULAR INFUSION LINE

(71) Applicant: Clearline MD, LLC, Woburn, MA (US)

(72) Inventors: Ihsan A. Haddad, Ashland, MA (US); David T. Healey, Lynnfield, MA (US)

(73) Assignee: Clearline MD, LLC, Woburn, MA (US)

( * ) Notice: Subject to any disclaimer, the term of this patent is extended or adjusted under 35 U.S.C. 154(b) by 465 days.

(21) Appl. No.: 15/047,071

(22) Filed: Feb. 18, 2016

(65) Prior Publication Data

US 2016/0158461 A1 Jun. 9, 2016

Related U.S. Application Data

(60) Division of application No. 13/842,837, filed on Mar. 15, 2013, now Pat. No. 9,604,014, which is a
(Continued)

(51) Int. Cl.
*A61M 5/36* (2006.01)
*A61M 5/168* (2006.01)

(52) U.S. Cl.
CPC .......... *A61M 5/365* (2013.01); *A61M 5/1685* (2013.01); *A61M 5/16813* (2013.01);
(Continued)

(58) Field of Classification Search
None
See application file for complete search history.

(56) References Cited

U.S. PATENT DOCUMENTS 2,850,211 A * 9/1958 Fernandez ............. A61M 5/14
222/159
3,929,157 A * 12/1975 Serur ................ A61M 5/16818
137/453
(Continued)

FOREIGN PATENT DOCUMENTS

EP 2890436 3/2019
EP 1768719 4/2019
(Continued)

*Primary Examiner* — Rebecca E Eisenberg
*Assistant Examiner* — Weng Lee
(74) *Attorney, Agent, or Firm* — Pandiscio & Pandiscio

(57) ABSTRACT

A system for detecting and removing a gas bubble from a vascular infusion line, the system comprising: a disposable cassette adapted for disposition intermediate the fluid line, the disposable cassette comprising: a body comprising an inlet port, a chamber, an outlet port, and a purge port, a first passageway connecting the inlet port to the chamber, the first passageway comprising a first bubble detection section where a gas bubble may be detected within the first passageway, a second passageway connecting the chamber with the outlet port, and a first pinch valve disposed along the second passageway intermediate the chamber and the outlet port, and a third passageway connecting the chamber with the purge port, the third passageway comprising a second bubble detection section where a gas bubble may be detected within the third passageway, and a second pinch valve disposed along the third passageway intermediate the chamber and the bubble detection section.

17 Claims, 50 Drawing Sheets

Related U.S. Application Data continuation-in-part of application No. 12/924,142, filed on Sep. 21, 2010, now Pat. No. 8,419,709, which is a continuation of application No. 11/134,894, filed on May 23, 2005, now Pat. No. 7,798,996.

(60) Provisional application No. 61/694,010, filed on Aug. 28, 2012, provisional application No. 60/630,471, filed on Nov. 23, 2004, provisional application No. 60/573,311, filed on May 21, 2004.

(52) U.S. Cl.
CPC ..... *A61M 5/16831* (2013.01); *A61M 2205/12* (2013.01); *A61M 2205/127* (2013.01); *A61M 2205/128* (2013.01); *A61M 2205/18* (2013.01); *A61M 2205/3313* (2013.01); *A61M 2205/3375* (2013.01); *A61M 2205/3592* (2013.01); *A61M 2205/50* (2013.01); *A61M 2205/581* (2013.01); *A61M 2205/587* (2013.01); *A61M 2205/8206* (2013.01)

(56) References Cited

U.S. PATENT DOCUMENTS

| | | |
|---|---|---|
| 3,949,745 A * | 4/1976 | Howell ............ A61M 5/1411 137/135 |
| 4,010,750 A * | 3/1977 | Howell ............ A61M 5/14 137/135 |
| 4,309,592 A | 1/1982 | Le Boeuf |
| 4,639,251 A * | 1/1987 | Kirkland ............ A61J 1/10 116/227 |
| 5,496,273 A | 3/1996 | Pastrone et al. |
| 5,616,124 A | 4/1997 | Hague et al. |
| 5,657,909 A * | 8/1997 | Barriac ............ B05B 11/0059 222/382 |
| 5,658,133 A | 8/1997 | Anderson et al. |
| 5,971,983 A | 10/1999 | Lesh |
| 6,012,457 A | 1/2000 | Lesh |
| 6,024,740 A | 2/2000 | Lesh et al. |
| 6,117,101 A | 9/2000 | Diederich et al. |
| 6,142,008 A | 11/2000 | Cole et al. |
| 6,231,320 B1 | 5/2001 | Lawless et al. |
| 6,245,064 B1 | 6/2001 | Lesh et al. |
| 6,254,599 B1 | 7/2001 | Lesh et al. |
| 6,261,283 B1 | 7/2001 | Morgan et al. |
| 6,293,926 B1 | 9/2001 | Sorensen et al. |
| 6,305,378 B1 | 10/2001 | Lesh |
| 6,383,151 B1 | 5/2002 | Diederich et al. |
| 6,416,511 B1 | 7/2002 | Lesh et al. |
| 6,471,697 B1 | 10/2002 | Lesh |
| 6,500,174 B1 | 12/2002 | Maguire et al. |
| 6,502,576 B1 | 1/2003 | Lesh |
| 6,514,249 B1 | 2/2003 | Maguire et al. |
| 6,535,689 B2 | 3/2003 | Augustine et al. |
| 6,547,788 B1 | 4/2003 | Maguire et al. |
| 6,572,349 B2 | 6/2003 | Sorensen et al. |
| 6,607,502 B1 | 8/2003 | Maguire et al. |
| 6,632,214 B2 | 10/2003 | Morgan et al. |
| 6,652,515 B1 | 11/2003 | Maguire et al. |
| 6,740,074 B2 | 5/2004 | Morgan et al. |
| 6,758,847 B2 | 7/2004 | Maguire |
| 6,775,473 B2 | 8/2004 | Augustine et al. |
| 6,855,144 B2 | 2/2005 | Lesh |
| 6,869,431 B2 | 3/2005 | Maguire et al. |
| 6,872,205 B2 | 3/2005 | Lesh et al. |
| 6,902,542 B2 | 6/2005 | Gordon |
| 6,932,114 B2 | 8/2005 | Sparks |
| 6,953,460 B2 | 10/2005 | Maguire et al. |
| 6,954,977 B2 | 10/2005 | Maguire et al. |
| 6,955,173 B2 | 10/2005 | Lesh |
| 6,962,488 B2 | 11/2005 | Davis et al. |
| 6,964,660 B2 | 11/2005 | Maguire et al. |
| 6,966,908 B2 | 11/2005 | Maguire et al. |
| 6,997,925 B2 | 2/2006 | Maguire et al. |
| 7,037,428 B1 | 5/2006 | Robinson et al. |
| 7,044,135 B2 | 5/2006 | Lesh |
| 7,115,205 B2 | 10/2006 | Robinson et al. |
| 7,241,295 B2 | 7/2007 | Maguire |
| 7,340,307 B2 | 3/2008 | Maguire et al. |
| 7,393,189 B2 | 7/2008 | Davis et al. |
| 7,695,423 B2 | 4/2010 | Robinson et al. |
| 7,720,362 B2 | 5/2010 | Arnold et al. |
| 7,798,996 B1 | 9/2010 | Haddad et al. |
| 7,803,217 B2 | 9/2010 | Arnold et al. |
| 7,806,863 B2 | 10/2010 | Haddad et al. |
| 7,806,864 B2 | 10/2010 | Haddad et al. |
| 7,927,302 B2 | 4/2011 | Arnold et al. |
| 7,983,540 B2 | 7/2011 | Arnold et al. |
| 7,993,337 B2 | 8/2011 | Lesh |
| 8,016,798 B2 | 9/2011 | Sparks et al. |
| 8,180,206 B2 | 5/2012 | Bieberich et al. |
| 8,241,409 B2 | 8/2012 | Arnold et al. |
| 8,385,731 B2 | 2/2013 | Arnold et al. |
| 8,419,709 B2 | 4/2013 | Haddad et al. |
| 8,444,592 B2 | 5/2013 | Williams et al. |
| 8,597,228 B2 | 12/2013 | Pyles et al. |
| 9,272,086 B2 | 3/2016 | Williams et al. |
| 9,604,014 B2 | 3/2017 | Haddad et al. |
| 2002/0016570 A1 | 2/2002 | Cartledge |
| 2003/0138349 A1 | 7/2003 | Robinson et al. |
| 2003/0159741 A1 | 8/2003 | Sparks |
| 2003/0199803 A1 | 10/2003 | Robinson et al. |
| 2005/0100450 A1 | 5/2005 | Bryant et al. |
| 2005/0118048 A1 | 6/2005 | Traxinger |
| 2007/0012623 A1 | 1/2007 | Robinson et al. |
| 2008/0269679 A1 | 10/2008 | Arnold et al. |
| 2009/0084721 A1 | 4/2009 | Yardimci et al. |
| 2011/0137237 A1 | 6/2011 | Prisco et al. |
| 2013/0092640 A1* | 4/2013 | Cassidy ............ A61M 5/36 210/801 |

FOREIGN PATENT DOCUMENTS

| | | |
|---|---|---|
| WO | WO 1993/009828 | 5/1993 |
| WO | WO 2002/019934 | 3/2002 |
| WO | WO 2004/108189 | 12/2004 |

* cited by examiner

SYSTEM FOR DETECTING AND REMOVING A GAS BUBBLE FROM A VASCULAR INFUSION LINE

REFERENCE TO PENDING PRIOR PATENT APPLICATIONS

This patent application is a division of U.S. patent application Ser. No. 13/842,837, filed Mar. 15, 2013 by Anesthesia Safety Products, LLC for SYSTEM FOR DETECTING AND REMOVING A GAS BUBBLE FROM A VASCULAR INFUSION LINE, which patent application:

(i) is a continuation-in-part of prior U.S. patent application Ser. No. 12/924,142, filed Sep. 21, 2010 by Ihsan A. Haddad et al. for SYSTEM FOR DETECTING AND REMOVING A GAS BUBBLE FROM A VASCULAR INFUSION LINE, which patent application is a continuation of prior U.S. patent application Ser. No. 11/134,894, filed May 23, 2005 by Ihsan A. Haddad et al. for SYSTEM FOR DETECTING AND REMOVING A GAS BUBBLE FROM A VASCULAR INFUSION LINE, which in turn claims benefit of (a) prior U.S. Provisional Patent Application Ser. No. 60/573,311, filed May 21, 2004 by Ihsan A. Haddad et al. for AIRTRAP ONE, and (b) prior U.S. Provisional Patent Application Ser. No. 60/630,471, filed Nov. 23, 2004 by Ihsan A. Haddad et al. for ANESTHESIA SAFETY PRODUCTS; and (ii) claims benefit of prior U.S. Provisional Patent Application Ser. No. 61/694,010, filed Aug. 28, 2012 by Ihsan A. Haddad et al. for METHOD AND APPARATUS FOR DETECTING AND REMOVING A GAS BUBBLE FROM A VASCULAR INFUSION LINE.

The above-identified patent applications are hereby incorporated herein by reference.

FIELD OF THE INVENTION

This invention relates to medical apparatus and procedures in general, and more particularly to medical apparatus and procedures for introducing a liquid into the vascular system of a patient.

BACKGROUND OF THE INVENTION

When a patient is undergoing a medical procedure that requires the infusion of a liquid into their circulatory system, be it venous or arterial, the introduction of a significantly-sized gas bubble (also known as a "gas volume", or a "gas bolus", etc.) into the patient's vascular system must be avoided, since the creation of a gas embolism can result in serious morbidity and even death.

There are two general categories of gas embolisms: venous and arterial. The primary difference between the two depends on the path by which the gas enters the vascular structure.

There are two general causes for the introduction of gas into either the arterial or venous systems:

(i) from instrumentation, such as accidental air injection through tubing, catheters, injectors, fluid warmers, etc.; and (ii) from physical conditions relating to the patient, such as sub-atmospheric pressure in incised non-collapsed veins or veins in a coagulated operative field, etc.

Available data indicates that 2+ cc's of air per kilogram of body weight, if injected into the venous system, is lethal. Smaller amounts can cause various degrees of morbidity. To put this in perspective, the air in an empty 4 ounce cup, if injected into the veins of a 170 pound person and not treated immediately, would typically prove lethal.

Thus, there is a need for a system for detecting and removing a gas bubble from a liquid infusion line prior to the gas bubble entering the vascular system of the patient.

SUMMARY OF THE INVENTION

The present invention provides a novel system for detecting and removing a gas bubble from a liquid infusion line before the gas bubble can enter the vascular system of the patient. Among other things, the system is adapted to stop the flow of fluid carrying the entrapped gas bubble, and to allow for the extraction of the gas bubble prior to permitting the fluid to enter the patient's circulatory system. In another aspect of the present invention, there is provided a novel method and apparatus for detecting a gas bubble in a fluid line, entrapping the gas bubble, and purging the gas bubble from the fluid line before the gas bubble can enter the patient's vascular system.

In another aspect of the present invention, there is provided a system for detecting and removing a gas bubble from a vascular infusion line, the system comprising:

a disposable cassette adapted for disposition intermediate the fluid line, the disposable cassette comprising:
    a body; and
    a flexible hollow tube having an inlet port being configured for connection to the supply side of the fluid line, an outlet port being configured for connection to the patient side of the fluid line and a purge port located intermediate the inlet port and the outlet port;

a base unit adapted to receive the disposable cassette and monitor fluid flow through the flexible hollow tube, wherein the base unit comprises:
    a sensor adapted to detect the presence of a gas bubble in the fluid flowing through the flexible hollow tube; and
    a pinch valve adapted to stop the flow of fluid through the flexible hollow tube; and an electronic control unit adapted to operate the base unit so that (i) fluid is permitted to flow past the pinch valve when no gas bubble is detected by the sensor; and (ii) fluid flow is arrested when a gas bubble is detected by the sensor.

In another aspect of the present invention, there is provided a system for detecting a gas bubble from a vascular infusion line, the system comprising:

a cassette adapted for disposition intermediate the fluid line, the cassette comprising:
    a body; and
    a passageway having an inlet port being configured for connection to the supply side of the fluid line, and an outlet port being configured for connection to the patient side of the fluid line; and
    a first portion of a valve for selectively arresting fluid flow through the passageway;

a base unit adapted to receive the cassette and monitor fluid flow through the passageway, wherein the base unit comprises:
    a sensor adapted to detect the presence of a gas bubble in the fluid flowing through the passageway; and
    a second portion of a valve for selectively arresting fluid flow through the passageway; and an electronic control unit adapted to operate the second portion of the valve so that (i) fluid is permitted to flow past the first portion of the valve when no gas bubble is detected by the sensor; and (ii) fluid flow is arrested when a gas bubble is detected by the sensor.

In another aspect of the present invention, there is provided a method for detecting and removing a gas bubble from a vascular infusion line, the method comprising:

providing a system comprising:
a disposable cassette adapted for disposition intermediate the fluid line, the disposable cassette comprising:
a body; and
a flexible hollow tube having an inlet port being configured for connection to the supply side of the fluid line, an outlet port being configured for connection to the patient side of the fluid line and a purge port located intermediate the inlet port and the outlet port;
a base unit adapted to receive the disposable cassette and monitor fluid flow through the flexible hollow tube, wherein the base unit comprises:
a sensor adapted to detect the presence of a gas bubble in the fluid flowing through the flexible hollow tube; and
a pinch valve adapted to stop the flow of fluid through the flexible hollow tube; and
an electronic control unit adapted to operate the base unit so that (i) fluid is permitted to flow past the pinch valve when no gas bubble is detected by the sensor; and (ii) fluid flow is arrested when a gas bubble is detected by the sensor;
initiating fluid flow through the disposable cassette; and
monitoring the fluid flowing through the disposable cassette for the occurrence of a gas bubble and, if a gas bubble is detected, arresting the flow of fluid through the fluid line.

In another aspect of the present invention, there is provided a method for detecting a gas bubble from a vascular infusion line, the method comprising:

providing a system comprising:
a cassette adapted for disposition intermediate the fluid line, the cassette comprising:
a body; and
a passageway having an inlet port being configured for connection to the supply side of the fluid line, and an outlet port being configured for connection to the patient side of the fluid line; and
a first portion of a valve for selectively arresting fluid flow through the passageway;
a base unit adapted to receive the cassette and monitor fluid flow through the passageway, wherein the base unit comprises:
a sensor adapted to detect the presence of a gas bubble in the fluid flowing through the passageway; and
a second portion of a valve for selectively arresting fluid flow through the passageway;
an electronic control unit adapted to operate the second portion of the valve so that (i) fluid is permitted to flow past the first portion of the valve when no gas bubble is detected by the sensor; and (ii) fluid flow is arrested when a gas bubble is detected by the sensor;
initiating fluid flow through the cassette; and
monitoring the fluid flowing through the cassette for the occurrence of a gas bubble and, if a gas bubble is detected, arresting the flow of fluid through the fluid line.

In another aspect of the present invention, there is provided a system for detecting and removing a gas bubble from a flexible vascular infusion line, the system comprising:

a cassette adapted for disposition intermediate the fluid line, the cassette comprising:
a body; and
a passageway having an inlet port being configured for connection to the supply side of the fluid line and an outlet port configured for connection to the patient side of the fluid line;
a base unit adapted to receive the cassette and monitor fluid flow through the passageway, wherein the base unit comprises:
a sensor adapted to detect the presence of a gas bubble in the fluid flowing through the passageway;
an electronic control unit disposed adjacent to the flexible fluid line, upstream of the cassette, wherein the electronic control unit comprises a valve for selectively arresting fluid flow through the flexible fluid line and circuitry for communicating with the sensor and operating the valve so that (i) fluid is permitted to flow through the flexible fluid line when no gas bubble is detected by the sensor; and (ii) fluid flow through the flexible fluid line is arrested when a gas bubble is detected by the sensor; and
a purge port located upstream of the patient and downstream of the electronic control unit.

In another aspect of the present invention, there is provided a method for detecting and removing a gas bubble from a flexible vascular infusion line, the method comprising:

providing a system comprising:
a cassette adapted for disposition intermediate the fluid line, the cassette comprising:
a body; and
a passageway having an inlet port being configured for connection to the supply side of the fluid line and an outlet port configured for connection to the patient side of the fluid line;
a base unit adapted to receive the cassette and monitor fluid flow through the passageway, wherein the base unit comprises:
a sensor adapted to detect the presence of a gas bubble in the fluid flowing through the passageway;
an electronic control unit disposed adjacent to the flexible fluid line, upstream of the cassette, wherein the electronic control unit comprises a valve for selectively arresting fluid flow through the flexible fluid line and circuitry for communicating with the sensor and operating the valve so that (i) fluid is permitted to flow through the flexible fluid line when no gas bubble is detected by the sensor; and (ii) fluid flow through the flexible fluid line is arrested when a gas bubble is detected by the sensor; and
a purge port located upstream of the patient and downstream of the electronic control unit;
initiating fluid flow through the flexible fluid line and through the cassette; and
monitoring the fluid flowing through the cassette for the occurrence of a gas bubble and, if a gas bubble is detected, arresting the flow of fluid through the flexible fluid line.

In another aspect of the present invention, there is provided a system for detecting and removing a gas bubble from a vascular infusion line, the system comprising:

a disposable cassette adapted for disposition intermediate the fluid line, the disposable cassette comprising:
a body comprising an inlet port, a chamber, an outlet port, and a purge port, a first passageway connecting the inlet port to the chamber, the first passageway comprising a first bubble detection section where a gas bubble may be detected within the first passageway, a second passageway connecting the chamber with the outlet port, and a first pinch valve disposed along the second passageway intermediate the chamber and the outlet port, and a third passageway connecting the chamber with the purge port, the third passageway comprising a second bubble detection section where a gas bubble may be detected within the third passageway, and a second pinch valve disposed along the third passageway intermediate the chamber and the bubble detection section.

In another aspect of the present invention, there is provided a method for detecting and removing a gas bubble from a vascular infusion line, the method comprising:

providing a system comprising:

a disposable cassette adapted for disposition intermediate the fluid line, the disposable cassette comprising:

a body comprising an inlet port, a chamber, an outlet port, and a purge port, a first passageway connecting the inlet port to the chamber, the first passageway comprising a first bubble detection section where a gas bubble may be detected within the first passageway, a second passageway connecting the chamber with the outlet port, and a first pinch valve disposed along the second passageway intermediate the chamber and the outlet port, and a third passageway connecting the chamber with the purge port, the third passageway comprising a second bubble detection section where a gas bubble may be detected within the third passageway, and a second pinch valve disposed along the third passageway intermediate the chamber and the bubble detection section;

connecting a fluid source to the inlet port of the disposable cassette, and connecting the outlet port of the disposable cassette; and allowing fluid to flow past the first pinch valve, and preventing fluid from flowing past the second pinch valve, when no gas bubble is detected by the first sensor; and preventing fluid from flowing past the first pinch valve, and allowing fluid to flow past the second pinch valve, when a gas bubble is detected by the first sensor.

In another aspect of the present invention, there is provided a collapsible chamber for preventing the entrapment of air in a fluid introduced into a patient, the collapsible chamber comprising a bladder having an inlet port for connection to a fluid source, an outlet port for connection to a patient, and a purge port for connection to a purge collector, the outlet port comprising an outlet port tube terminating in an outlet port mouth, the purge port comprising a purge port tube terminating in a purge port mouth, and a float disposed within the bladder, the float being connected to the outlet port tube and the purge port tube such that when an appropriate level of fluid is present in the bladder, the outlet port mouth is connected to the fluid and the purge port mouth is disposed above the fluid, and when an appropriate level of fluid is not present in the bladder, the float closes off the outlet port mouth.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

System with Disposable Cassette

The present invention provides a novel system for detecting a gas bubble in a fluid line, entrapping the gas bubble, and purging the gas bubble before the gas bubble can enter the patient's vascular system.

In one preferred form of the invention, the novel system comprises three components: (i) a disposable cassette for disposition intermediate the fluid line, wherein fluid flowing through the disposable cassette may be monitored and, if a gas bubble is detected within the fluid flow, the fluid flow may be stopped and the gas bubble removed before continuing the fluid flow; (ii) a base unit providing apparatus for monitoring the fluid flow through the disposable cassette and, if a gas bubble is detected, selectively stopping the fluid flow through the disposable cassette while the gas bubble is removed; and (iii) an electronic control unit for operating the base unit.

Figure 1:
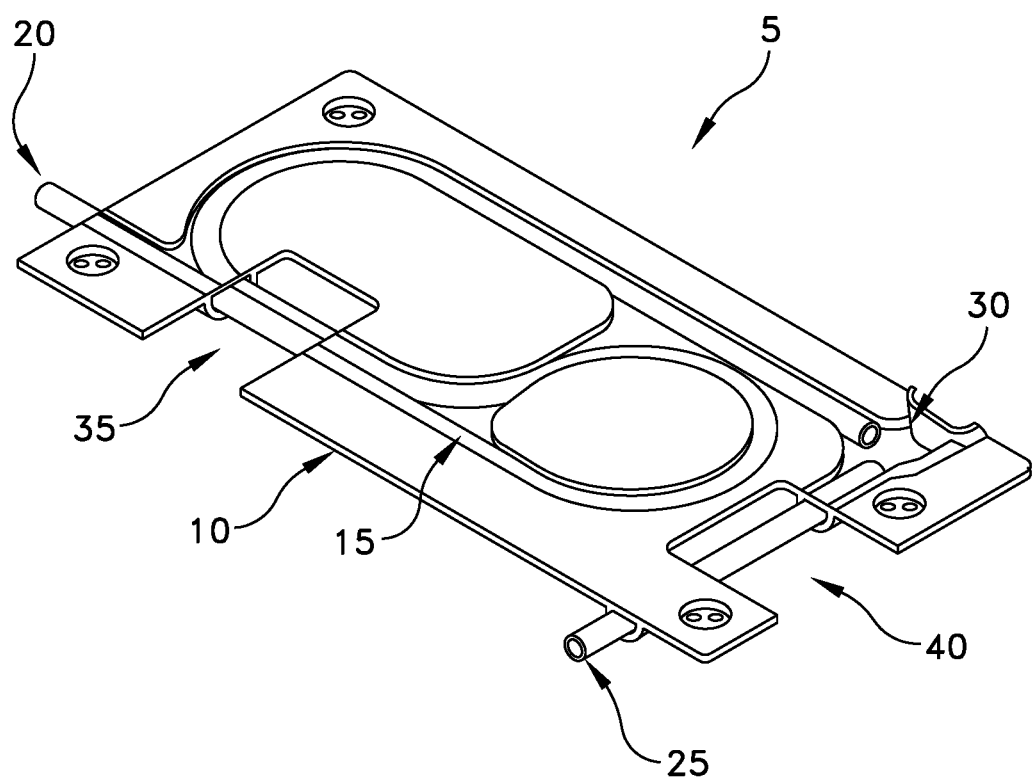
FIG. 1 is a schematic view showing a disposable cassette formed in accordance with the present invention.
Figure 2:
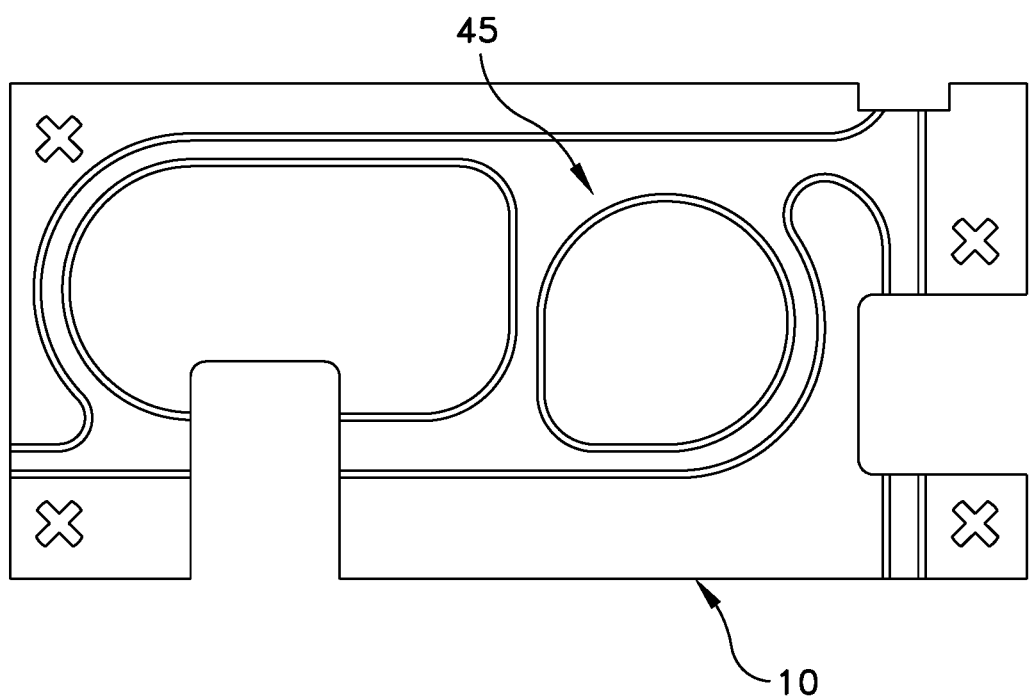
FIGS. 2-4 are schematic views showing components of the disposable cassette shown in FIG. 1.
Figure 3:
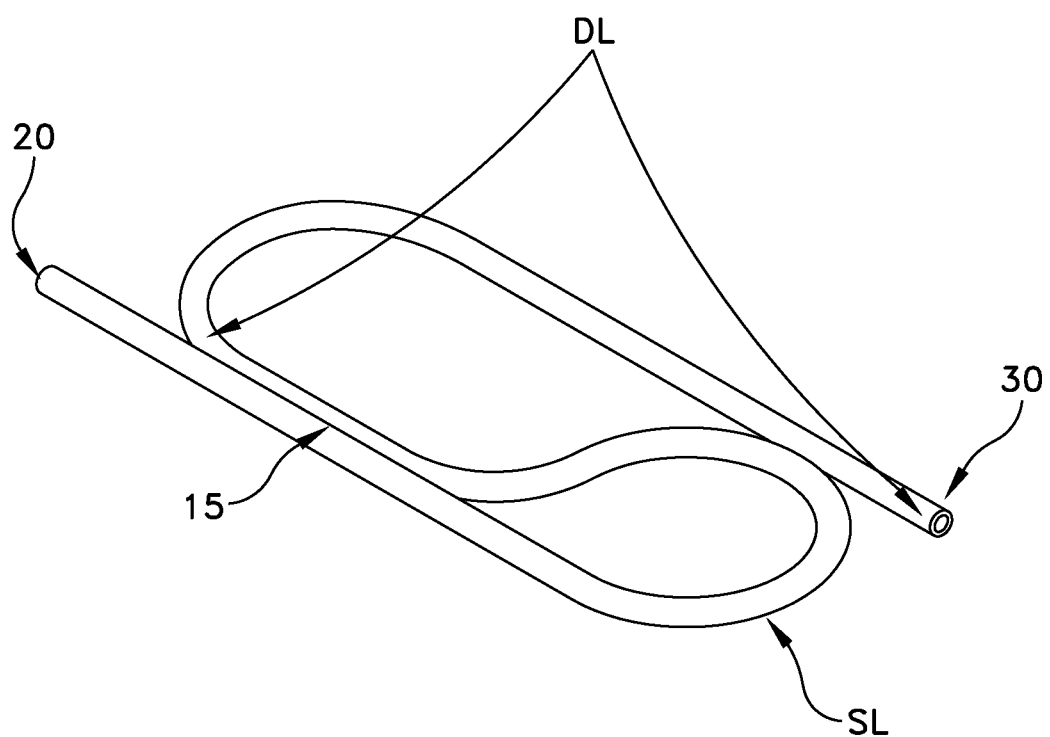
Figure 4:
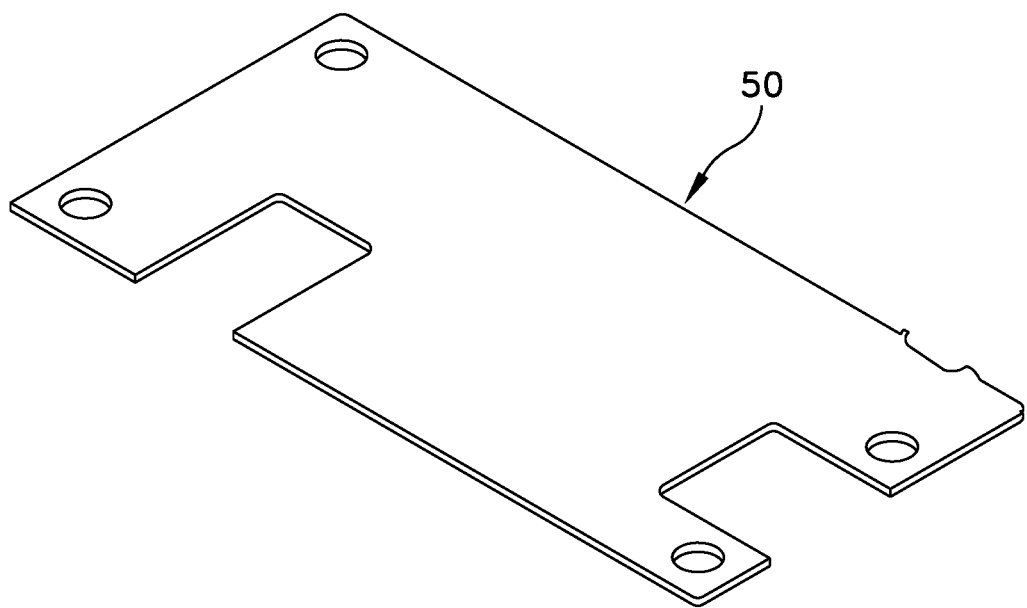
Figure 5:
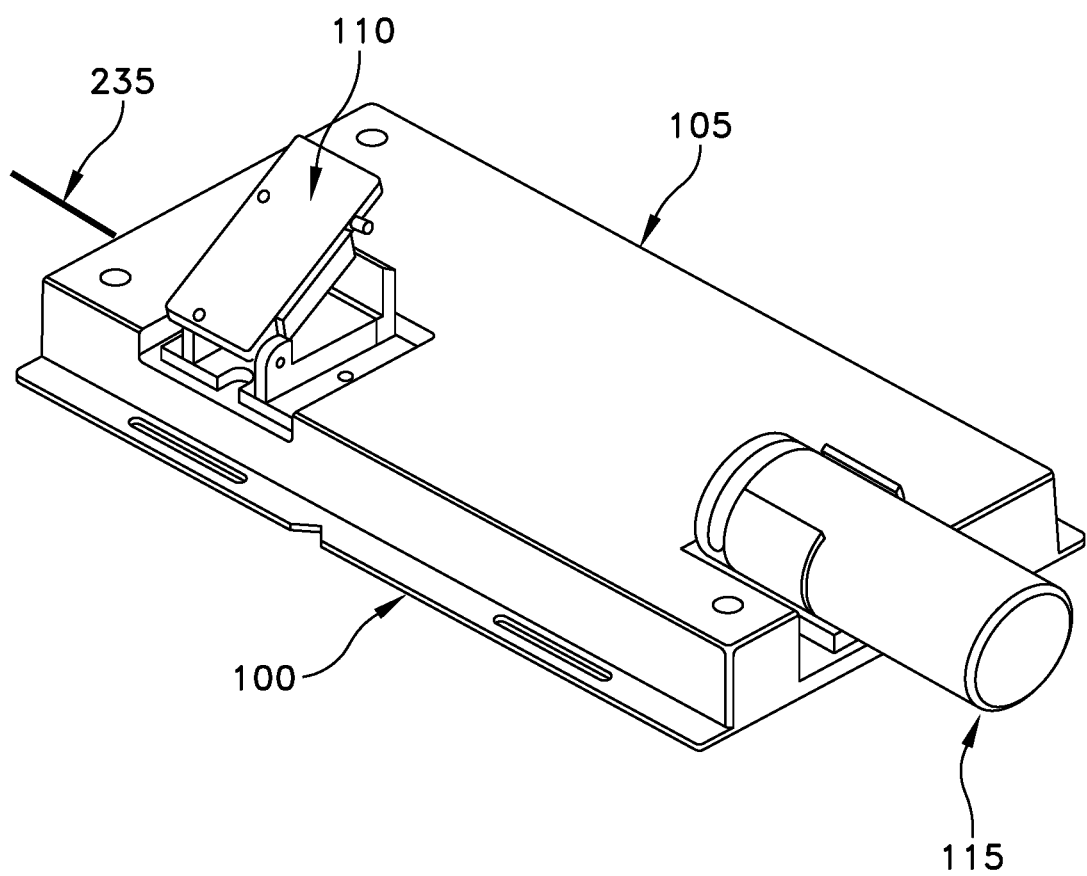
FIG. 5 is a schematic view showing a base unit formed in accordance with the present invention.
Figure 6:
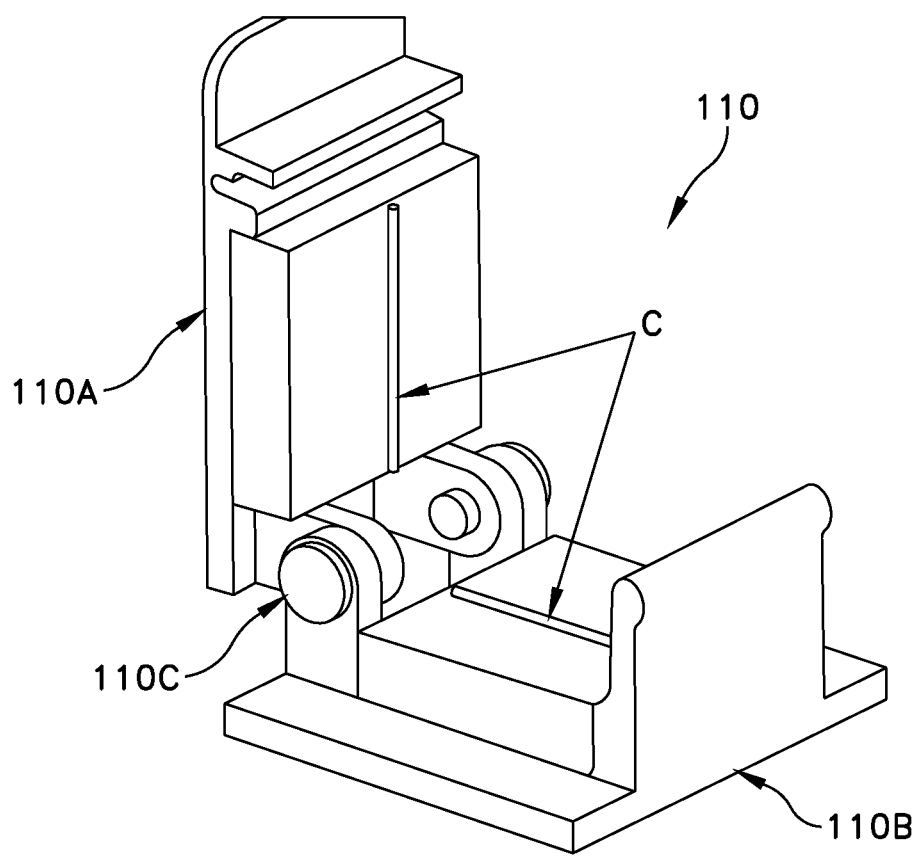
FIG. 6 is a schematic view showing a component of the base unit shown in FIG. 5.

More particularly, and looking now at FIGS. 1-4, there is shown a disposable cassette 5 which comprises one preferred form of the invention. Disposable cassette 5 is adapted for disposition intermediate the fluid line (e.g., an IV line), wherein fluid flowing through the disposable cassette may be monitored and, if a gas bubble (e.g., an air bubble) is detected within the fluid flow, the fluid flow may be stopped and the gas bubble removed before continuing the fluid flow. Disposable cassette 5 comprises a body 10 including tubing 15 (FIG. 1). Tubing 15 has an inlet port 20, and outlet port 25, and a purge port 30. Body 10 and tubing 15 are arranged so that tubing 15 is exposed at a sensor station 35 and at a pinch location 40 (e.g., with openings). Inlet port 20 and outlet port 25 are configured with an appropriate fitting (i.e., Luer, male, female, locking "T", stopcock, etc.) so that the tubing 15 of the disposable cassette 5 can be connected intermediate a fluid line entering the patient. Purge port 30 provides selective access (e.g., via a removable cap) to the interior of tubing 15, whereby to permit removal of a gas bubble in the fluid line, as will hereinafter be discussed. In one preferred form of the invention, disposable cassette 5 can be formed by providing a groove 45 in body 10 (FIG. 2), wherein groove 45 is configured to receive tubing 15 (FIG. 3), with a cover 50 (FIG. 4) securing the tubing 15 within groove 45.

Body 10 and cover 50 are preferably formed out of medical grade, soft or semi-soft, sterilizable, clear or transparent or semi-transparent, plastic such as PVC, a urethane, etc.

Tubing 15 is preferably a clear plastic FDA Class 6 tubing with a durometer consistent with the "pinch" requirements of the base unit's pinch valve, as will hereinafter be discussed. Tubing 15 is sized so as to be consistent with the flow requirements of the IV fluid line. By way of example but not limitation, for adults and high flow IV requirements, a tube 15 having a ⅛ inch inside diameter, and a 3/16 inch outside diameter, may be used.

Preferably the disposable cassette 5 is provided to the user in a pre-assembled form (i.e., with tubing 15 loaded into groove 45 and sealed in place with cover 50), with the disposable cassette being sealed in a sterilized package which is opened at the time of use.

Figure 7:
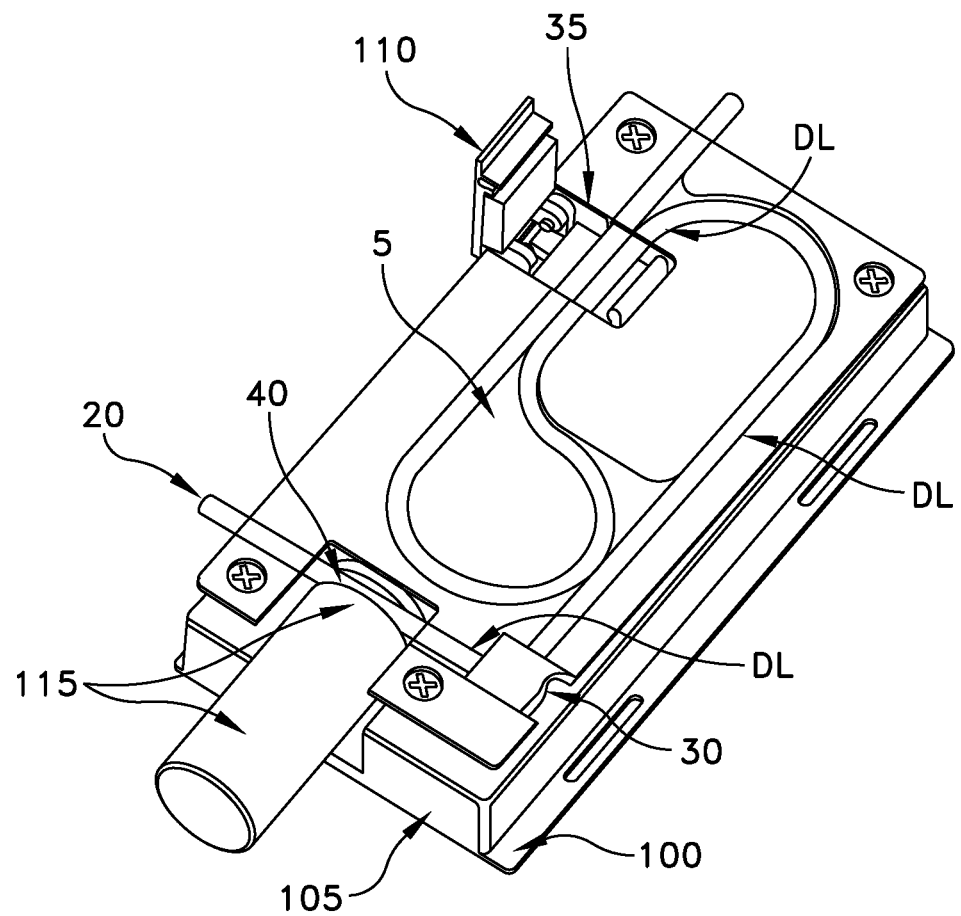
FIGS. 7 and 8 are schematic views showing the disposable cassette of FIG. 1 mounted on the base unit of FIG. 5.
Figure 8:
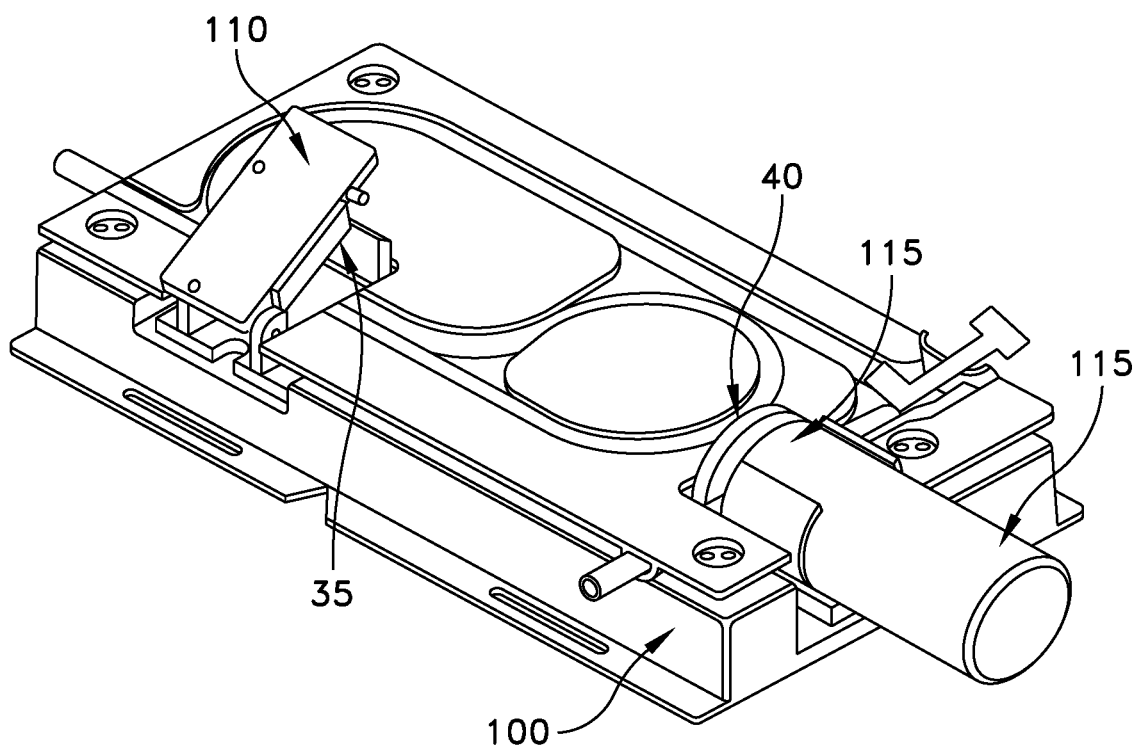

Looking next at FIGS. 5-9, there is shown a base unit 100 which comprises one preferred form of the invention. Base unit 100 is adapted to receive disposable cassette 5 and monitor the fluid flow through the disposable cassette and, if a gas bubble is detected, selectively stop the fluid flow through the disposable cassette while the gas bubble is removed. Base unit 100 generally comprises a seat 105 (FIG. 5) for seating the disposable cassette 5. Base unit 100 also comprises a sensor 110 for detecting the presence of a gas bubble in the fluid flowing through tubing 15 of the disposable cassette. In one form of the invention, sensor 110 comprises an ultrasound sensor (FIG. 6) and, in one particularly preferred form of the invention, sensor 110 comprises an ultrasound sensor having two halves 110A, 110B hinged together at 110C. Each half 110A, 110B comprises an appropriate rectangular ultrasound crystal C running the length of the face. Base unit 100 also comprises a pinch valve 115 (FIG. 5) for selectively pinching off the tubing 15 of disposable cassette 5, whereby to selectively stop fluid flow through the tubing. By way of example but not limitation, pinch valve 115 may comprise a solenoid having a movable member for (i) engaging the tubing 15 when the movable member is placed into its extended position, whereby to pinch the tubing 15 closed, and (ii) disengaging the tubing 15 when the movable member is placed into its retracted position, whereby to allow the tubing to expand to its full diameter. As seen in FIGS. 7 and 8, disposable cassette 5 and base unit 100 are constructed so that when disposable cassette 5 is received on seat 105, sensor station 35 of disposable cassette 5 is positioned adjacent to sensor 110 of base unit 100, and pinch location 40 of disposable cassette 5 is disposed adjacent to pinch valve 115 of base unit 100.

Figure 9:
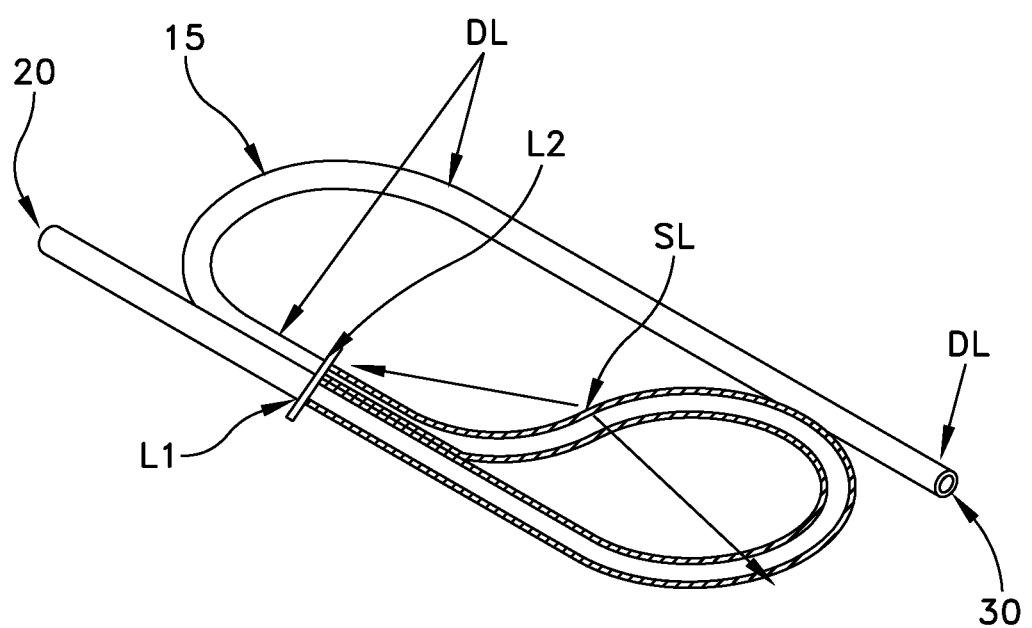
FIG. 9 is a schematic view showing the disposable cassette's sensor loop and delay loop.

Significantly, and as will hereinafter be discussed in further detail, due to the switchback configuration of the tubing 15 of disposable cassette 5, two legs of tubing 15 will pass by sensor 110 at sensor station 35 (FIGS. 7 and 9). Thus, tubing 15 will be monitored by sensor 110 at two locations, L1 and L2. The length of tubing 15 extending between the two locations L1 and L2 may be referred to as the "sensor loop" SL.

Furthermore, it will be appreciated that a length of tubing extends between sensor location L2 and purge port 30. This length of tubing provides a "delay loop" DL which will hereinafter be discussed.

Figure 10:
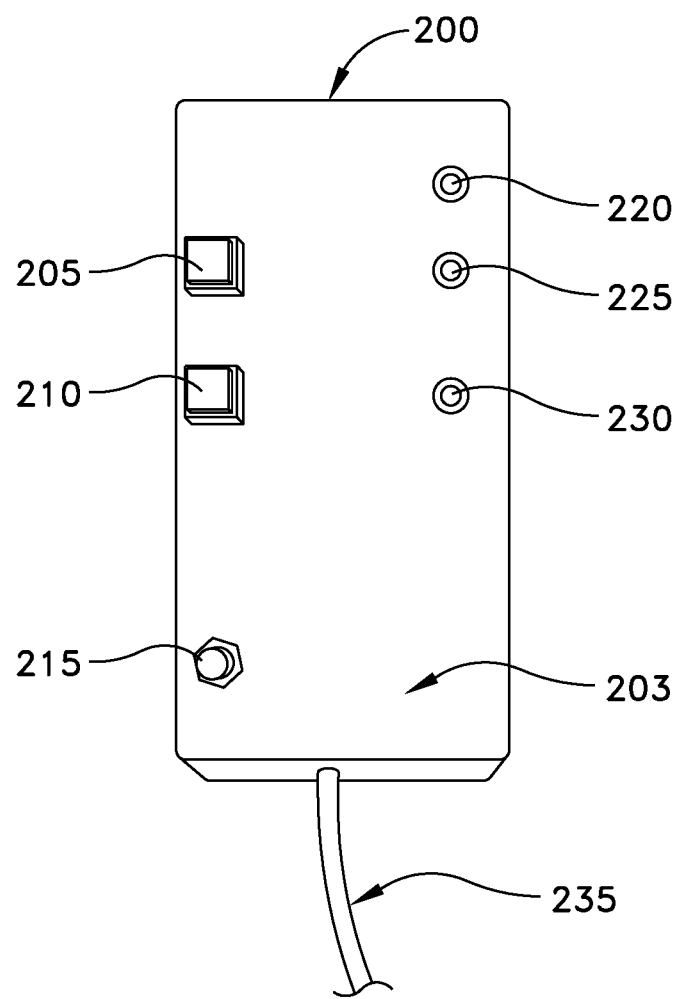
FIG. 10 is a schematic view showing an electronic control unit formed in accordance with the present invention.
Figure 11:
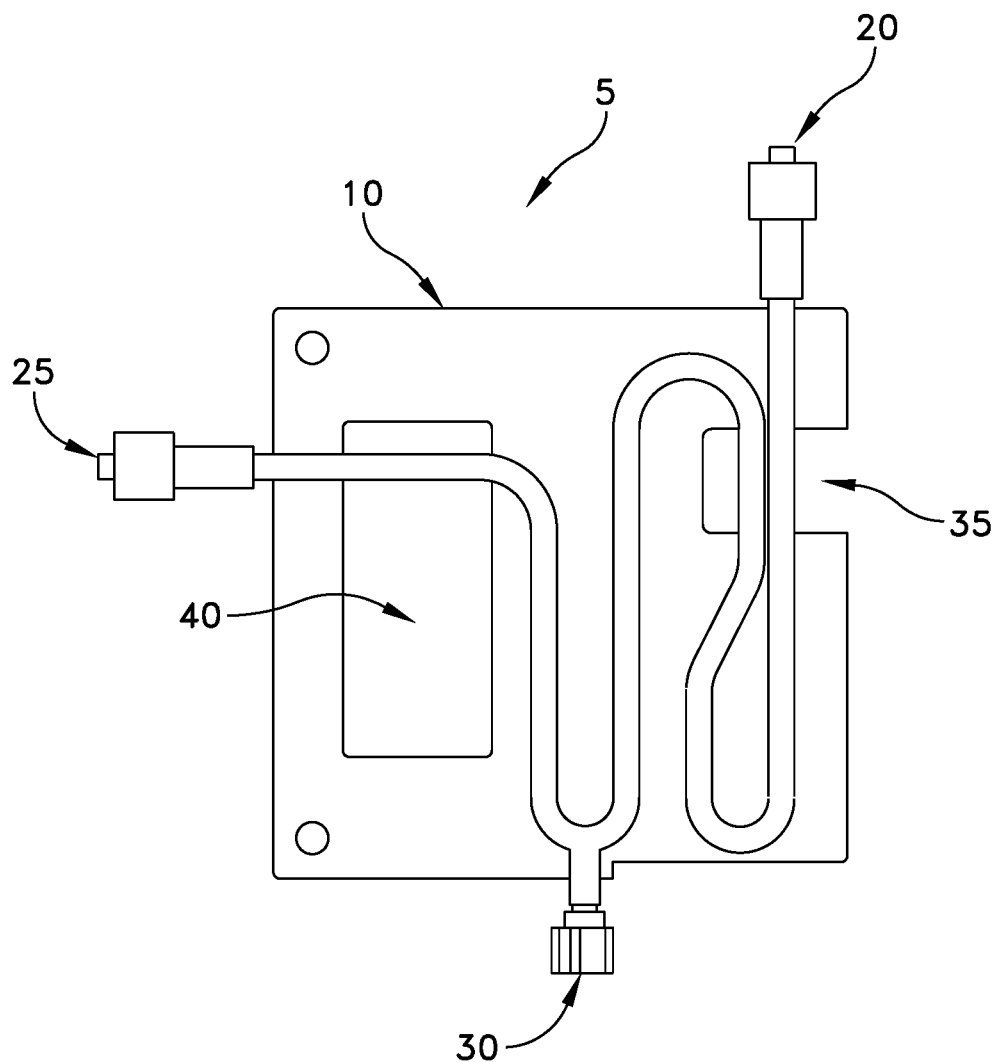
FIG. 11 is a schematic view showing an alternative form of the disposable cassette.
Figure 12:
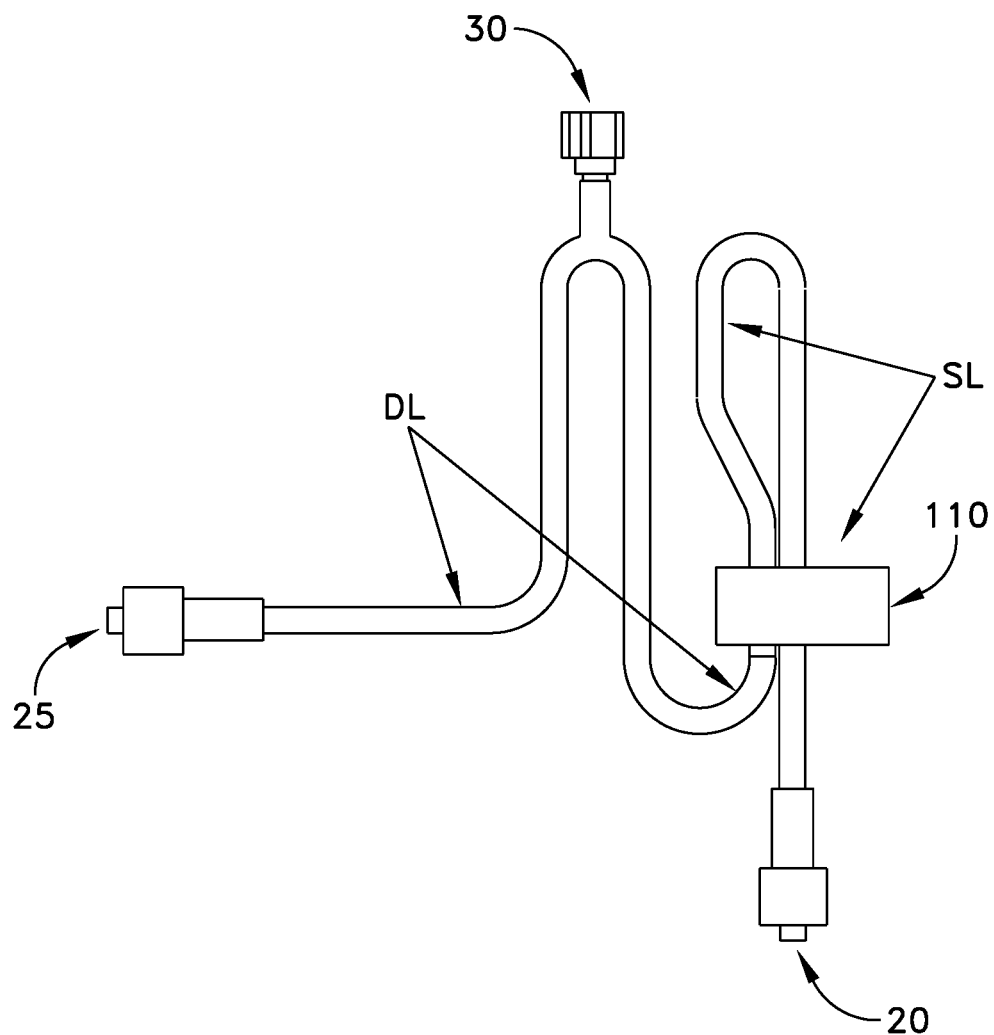
FIG. 12 is a schematic view showing the tubing component of the disposable cassette shown in FIG. 11.
Figure 13:
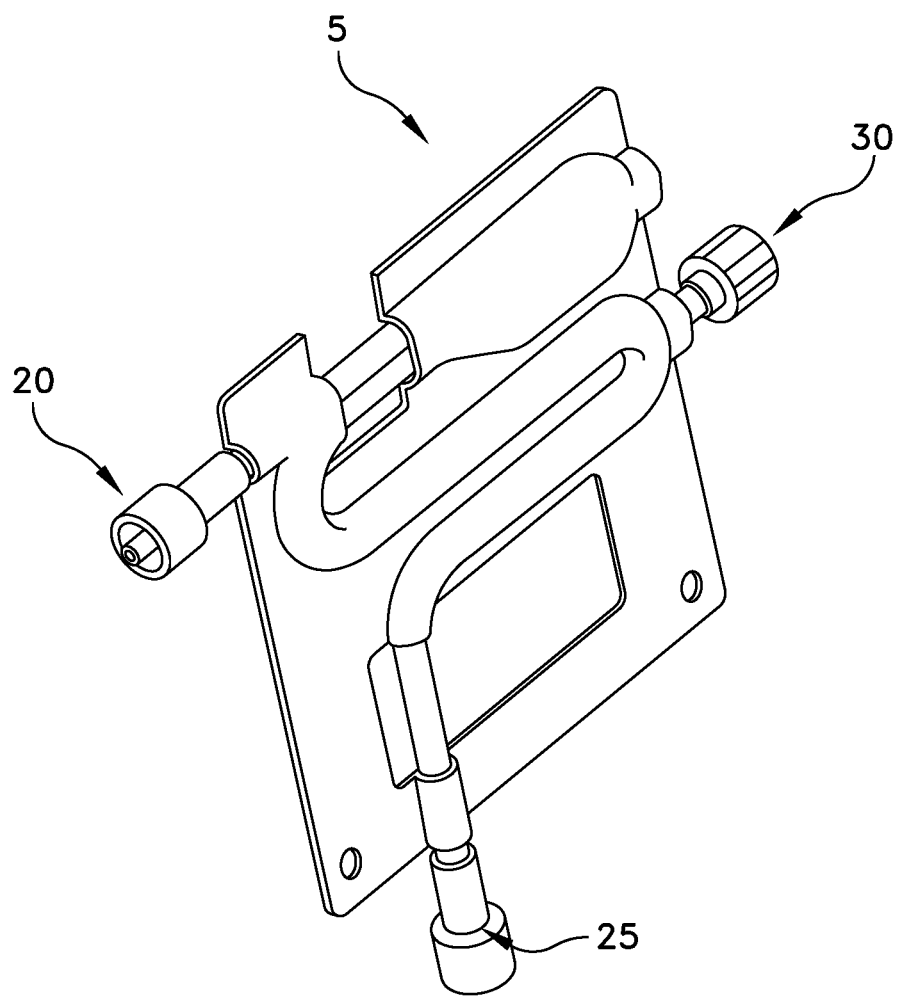
FIG. 13 is another schematic view of the disposable cassette shown in FIG. 11.
Figure 14:
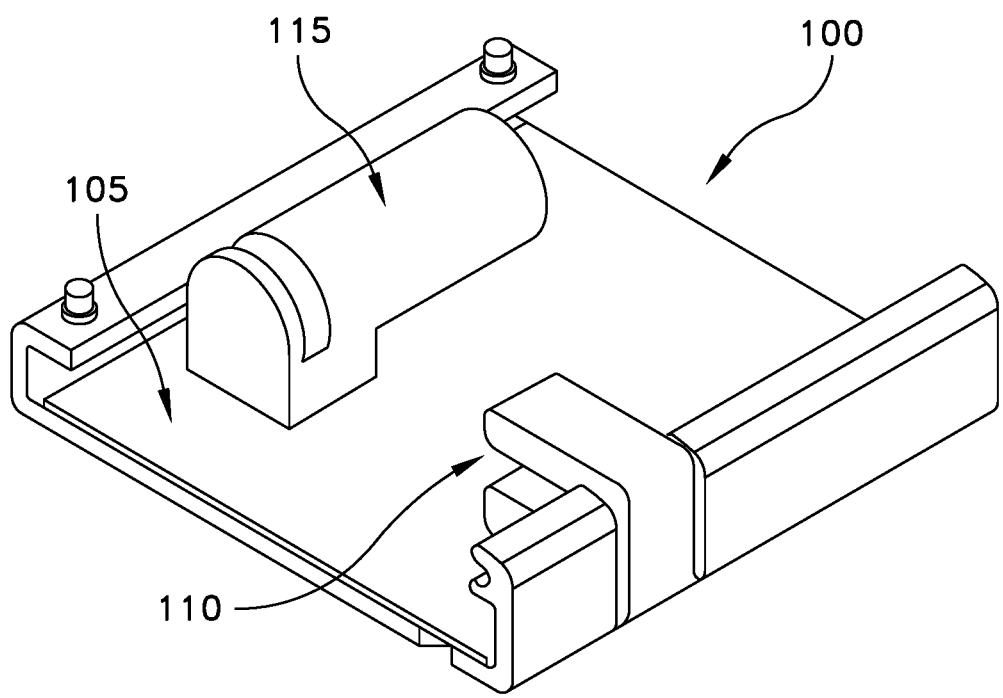
FIG. 14 is a schematic view showing an alternative form of base unit.
Figure 15:
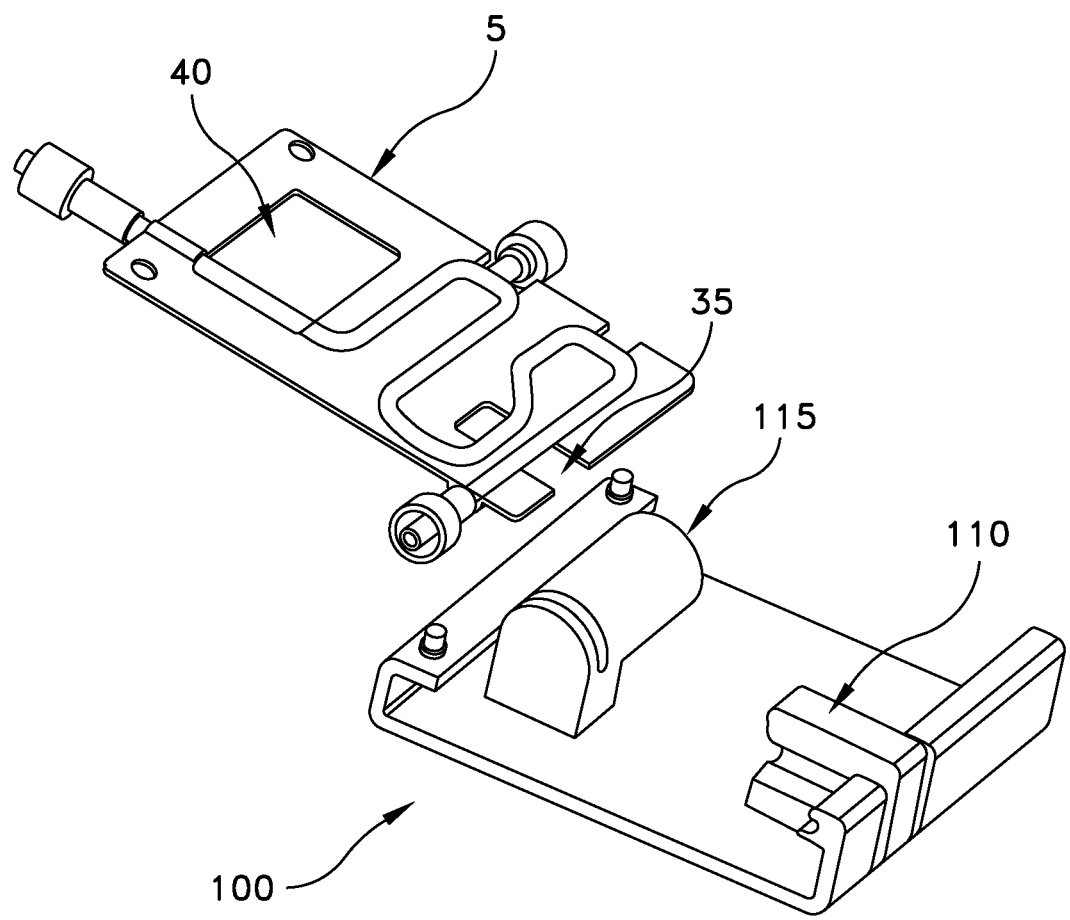
FIGS. 15 and 16 are schematic views showing the disposable cassette of FIGS. 11 and 13 in conjunction with the base unit of FIG. 14.
Figure 16:
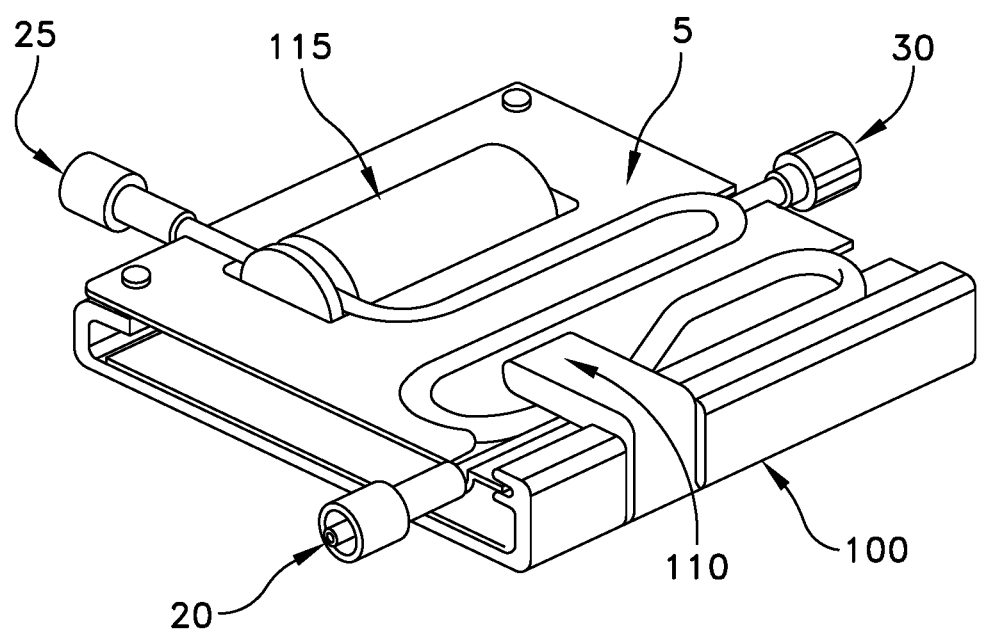
Figure 17:
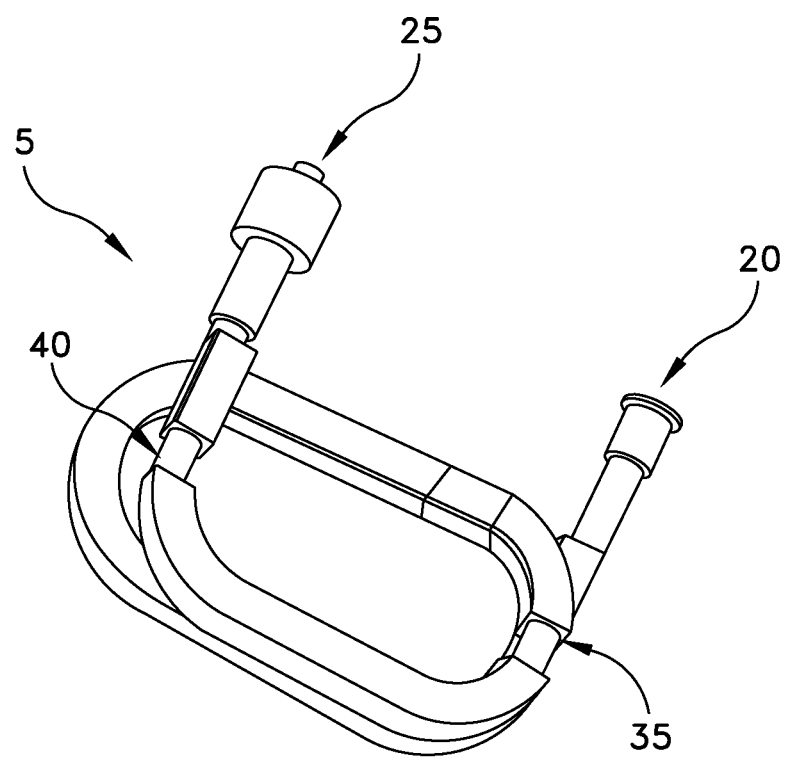
FIGS. 17 and 18 are schematic views showing an alternative form of the disposable cassette.
Figure 18:
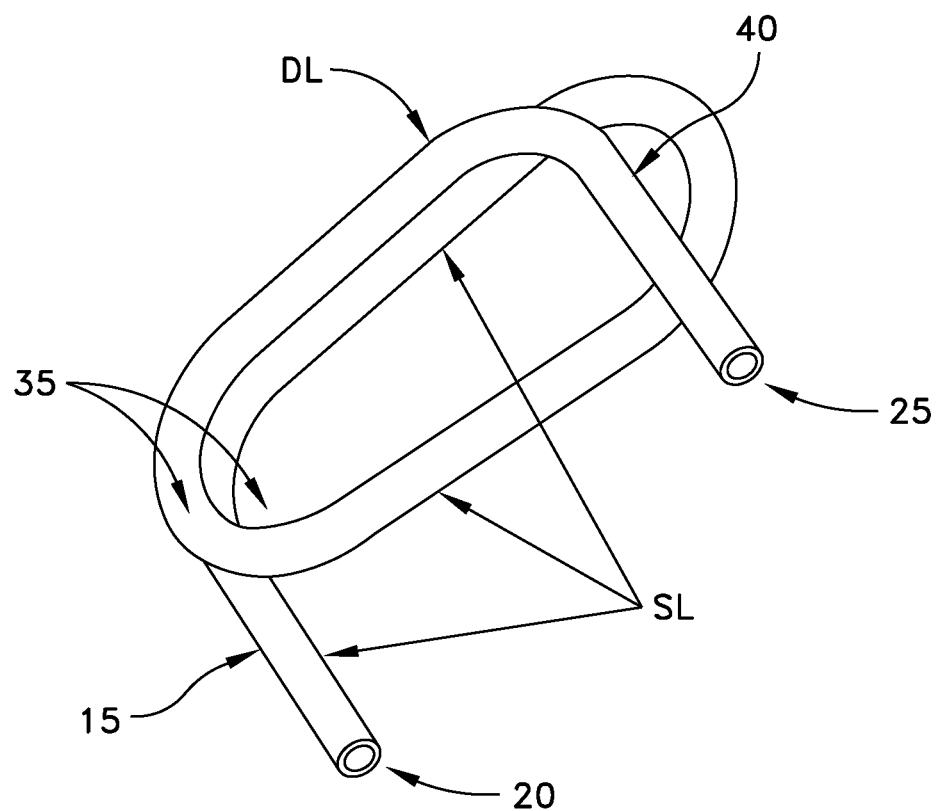
Figure 19:
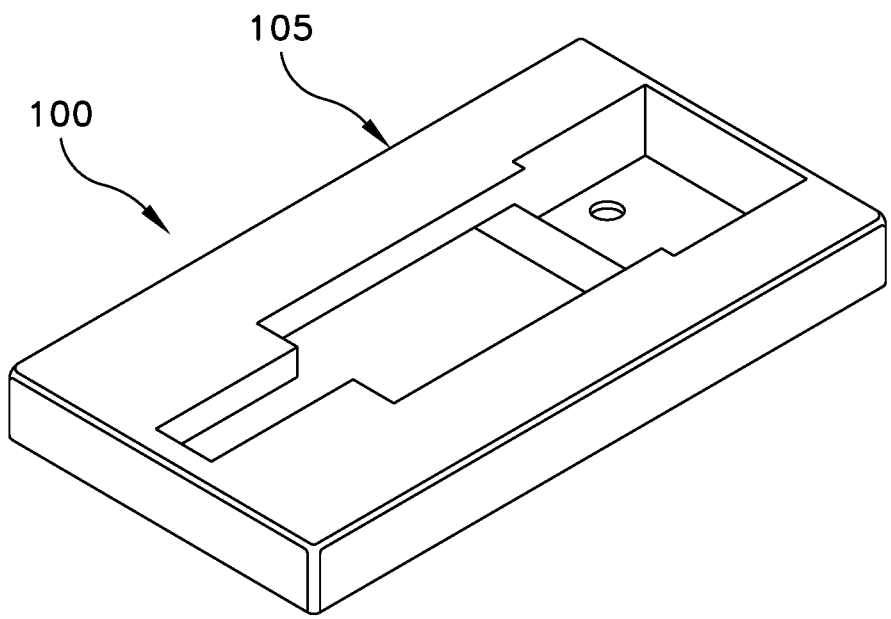
FIGS. 19 and 20 are schematic views showing an alternative form of the base unit.
Figure 20:
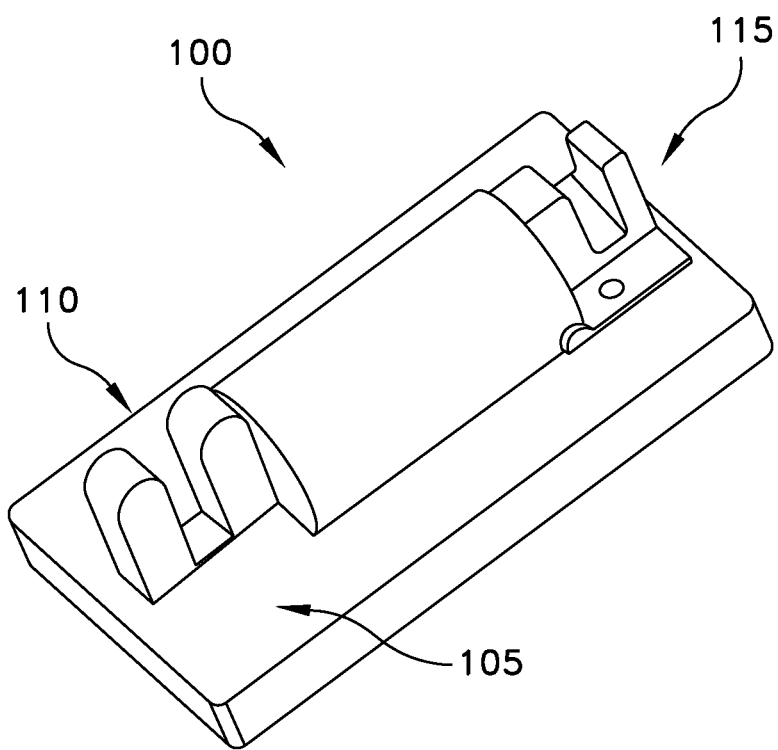
Figure 21:
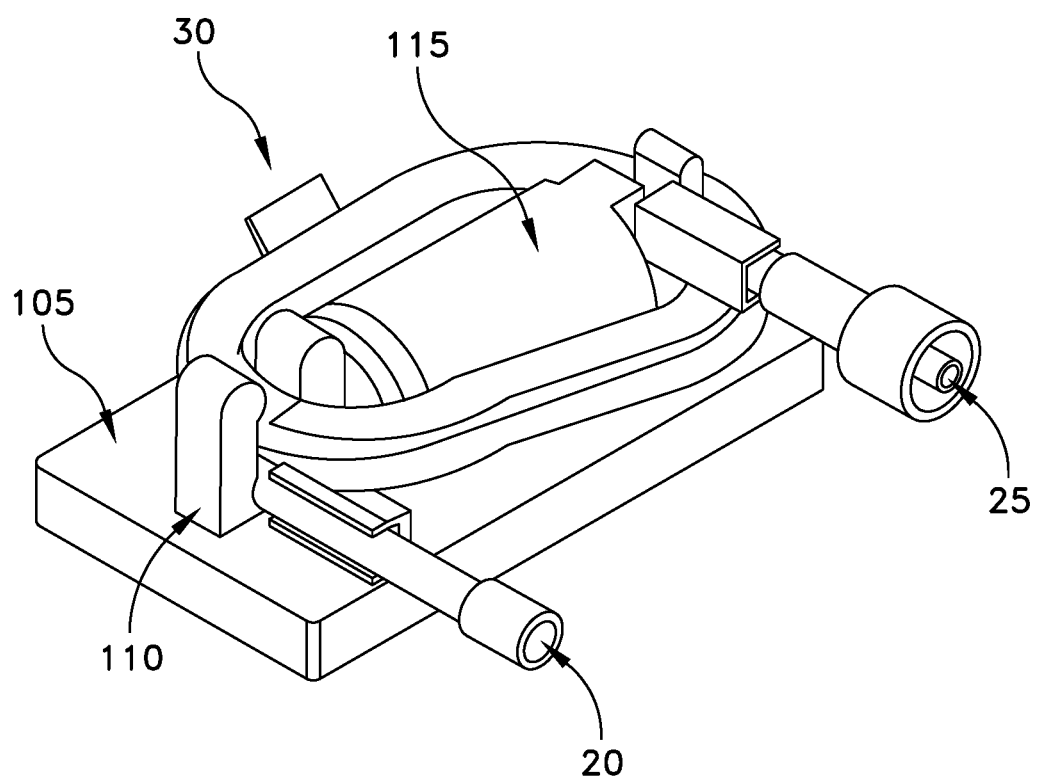
FIG. 21 is a schematic view showing the disposable cassette of FIGS. 17 and 18 in conjunction with the base unit of FIGS. 19 and 20.

Looking next at FIG. 10, there is shown an electronic control unit 200 which comprises one preferred form of the invention. Electronic control unit 200 is adapted to operate base unit 100 as will hereinafter be discussed. Electronic control unit 200 generally comprises a housing 203, an on/off switch 205, a sound off switch 210, a system reset switch 215, a green light 220, a system red light 225, a sound red light 230, an umbilical cord 235 for connecting electronic control unit 200 to base unit 100, and various conventional electronic components (not shown) housed by housing 203 and adapted to operate as will hereinafter be discussed.

Among other things, umbilical cord 235 connects electronic control unit 200 to the base unit's sensor 110 whereby to operate (i.e., power and read) the same, and umbilical cord 235 connects electronic control unit 200 to the base unit's pinch valve 115, whereby to operate (i.e., power and control) the same.

Electronic control unit 200 is preferably internally powered by a 12 volt rechargeable battery pack, although it may also be powered by an external power source, e.g., by connection to a wall plug.

In operation, a disposable cassette 5 is withdrawn from its sterilized package and loaded into base unit 100. This is done by opening sensor 110, seating disposable cassette 5 on the base unit's seat 105 so that the cassette's sensor station 35 is located adjacent to the base unit's sensor 110 and so that the disposable cassette's pinch location 40 is located adjacent to the base unit's pinch valve 115, and then closing sensor 110.

Next, the "source side" of a fluid line (e.g., an IV line) is connected to the cassette's inlet port 20, and the cassette's output port 25 is connected to the "patient side" of the IV line.

The IV line is then primed, air removed, etc. so that the fluid line is ready to infuse the patient.

Then the system is turned on by pushing on/off switch 205.

Next, fluid is allowed to flow from the fluid source into tubing 15 of disposable cassette 5. As the fluid flows through the tubing, sensor 110 monitors the fluid flow, sensing for the presence of a gas bubble. So long as no gas bubble is detected, the fluid is allowed to flow uninterrupted, thereby infusing the patient with the desired fluid. Green light 220 is lit when the system is on and no gas bubble is detected by sensor 110.

In the event that sensor 110 detects the presence of a gas bubble (e.g., an air bubble) in the fluid, electronic control unit 200 turns on red light 225, sounds an audible alarm in electronic control unit 200, and activates pinch valve 115, thereby arresting the fluid flow.

The operator can now activate the sound off switch 210, temporarily turning the alarm sound off, and then use purge port 30 to bleed the gas bubble from the system. As soon as the sensor no longer detects a gas bubble at sensor station 35, indicating that the gas bubble has been purged from the line, green light 220 comes back on, signifying that the system may now be reset. The operator then actuates system reset switch 215, thereby resetting the system. Upon system reset, pinch valve 115 is re-opened, thereby permitting the fluid flow to resume.

In the event that the sound off switch 210 is pushed, but the system fault is not corrected within some specified time period (e.g., one minute), the electronic control unit 200 then turns the sound alarm back on.

In the event that the reset switch 215 is activated, but the fault condition is not corrected, the system will not reset.

It should be appreciated that, as noted above, the disposable cassette's tubing 15 passes by sensor 110 at two locations, i.e., L1 and L2.

If desired, the system can be configured such that sensor 110 and electronic control unit 200 trigger a fault condition when a gas bubble is detected at either location L1 or L2.

More preferably, however, the system is configured such that sensor 110 and electronic control unit 200 trigger a fault condition only when a gas volume is simultaneously detected at both locations L1 and L2. This configuration can be advantageous, inasmuch as simultaneously detecting a gas bubble at both locations L1 and L2 can be indicative of the presence of a large gas bubble in the fluid line, i.e., one completely filling the sensor loop SL. As a result, by configuring the disposable cassette 5 so that its sensor loop SL is of a pre-determined size, the system can discriminate between gas bubbles of different sizes, activating the fault condition only when the gas bubble exceeds a certain size. In other words, in this form of the invention, the length of the sensor loop SL, and its internal volume, determines the amount of gas that can be present in the circuit before the fault condition is triggered. This feature can be advantageous, inasmuch as adults may be capable of safely tolerating a larger gas bubble than an infant, etc. Furthermore, gas bubbles commonly exist in most IV circuits; tiny gas bubbles are generally deemed harmless, and it is only the larger gas bubbles which are considered to pose a threat to the patient. By making the system capable of discriminating between different bubble sizes when determining a fault condition, false positives can be minimized without sacrificing system usefulness.

In one preferred form of the invention, sensor loop SL is configured to have a volume of 1 cc.

It should also be appreciated that various system components typically have response time delays associated with them. Thus, for example, there is typically a delay between when a fault condition occurs at locations L1 and/or L2, and when the fault condition is detected by sensor 110, and when the pinch valve 115 can be closed. To this end, it is advantageous to provide a delay loop DL between sensor station 35 and purge port 30. By properly setting the length of delay loop DL relative to the aggregated response delay times of the system components, the system can be provided with the capacity to timely stop the fluid flow and reliably trap the undesirable gas volume in the delay loop for safe removal of the same.

In one preferred form of the invention, delay loop DL is configured to have a length of 10 cm.

Disposable cassette 5 is preferably discarded after use.

Looking next at FIGS. 11-16, there are shown alternative constructions for disposable cassette 5 and base unit 100. Among other things, this form of the invention utilizes (i) a different and more compact geometry than that shown in FIGS. 1-10; (ii) a one-piece sensor 110; and (iii) a vacuum-formed cassette body 10 which encompasses portions of tubing 15, whereby to eliminate the use of body grooves 45 and cover 50.

Looking next at FIGS. 17-21, there are shown other alternative constructions for disposable cassette 5 and base unit 100. Among other things, this form of the invention utilizes (i) a different and more compact geometry than that shown in FIGS. 1-16; (ii) a disposable cassette 5 omitting the large planar body 10 and cover 50, with tubing 15 in the form of an inline stacked configuration and secured together (e.g., with glue, molding techniques, etc.) so as to form the structure of disposable cassette 5 (here, the securing structure can be thought of as constituting the body 10); and (iii) a base unit 100 modified to receive the modified disposable cassette 5.

Figure 22:
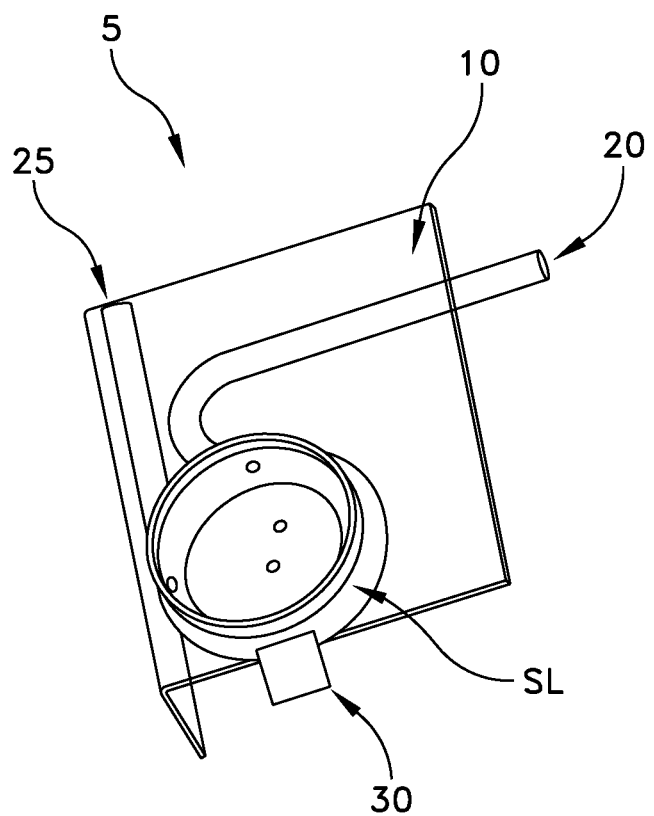
FIG. 22 is a schematic view showing an alternative form of the disposable cassette.
Figure 23:
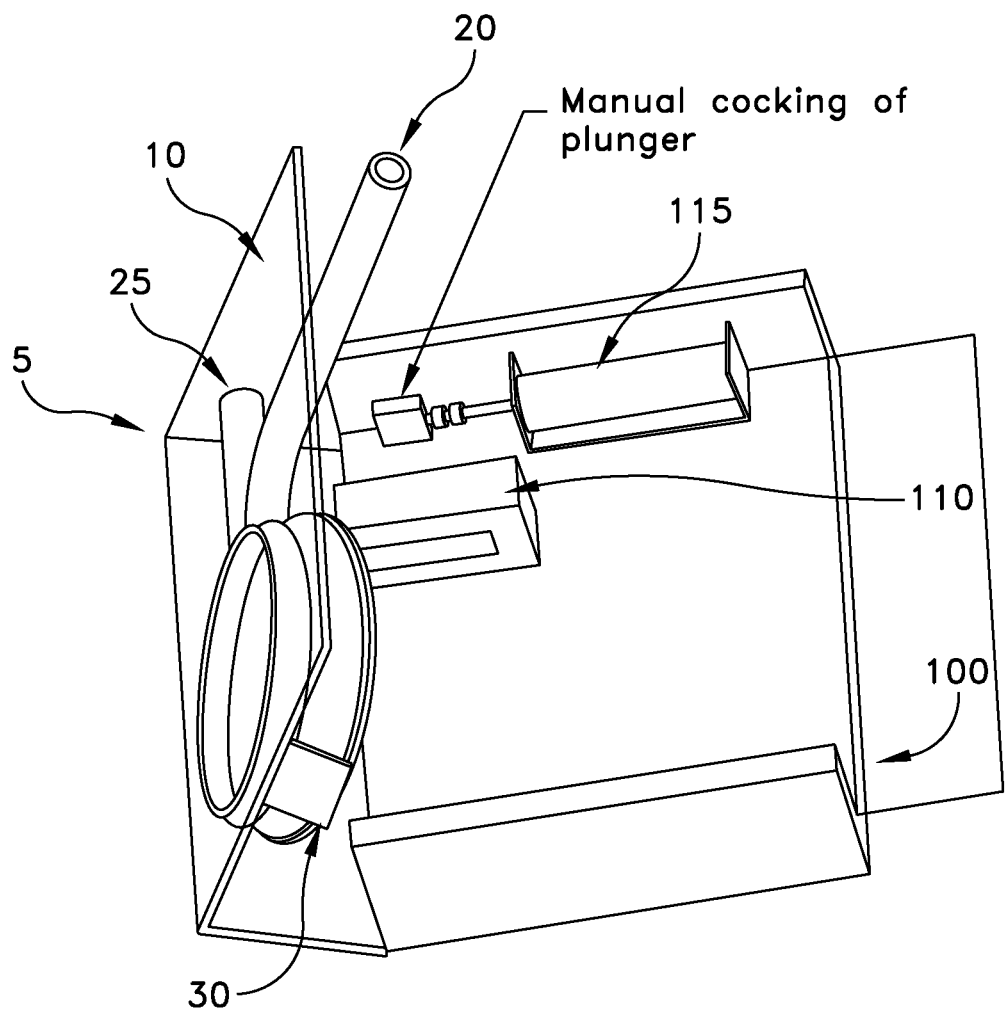
FIGS. 23 and 24 are schematic views showing the disposable cassette of FIG. 22 in conjunction with an alternative base unit.
Figure 24:
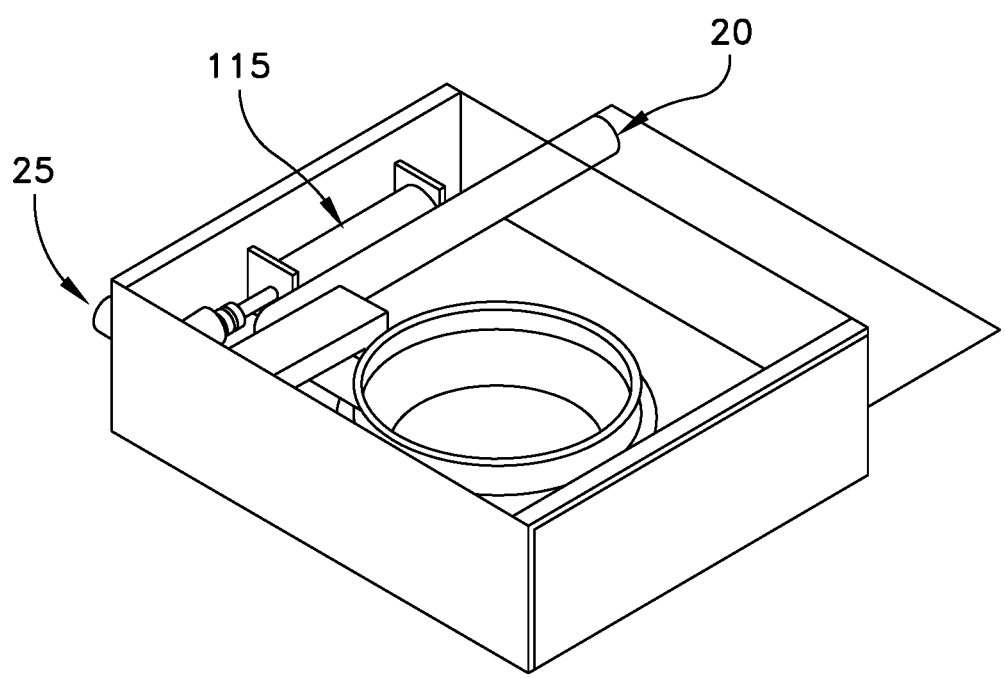

Looking next at FIGS. 22-24, there are shown further alternative constructions for disposable cassette 5 and base unit 100. Among other things, this form of the invention utilizes (i) a different and more compact geometry than that shown in FIGS. 1-21; (ii) a disposable cassette 5 having an L-shaped body 10, with tubing 15 in the form of an inline stacked coil configuration and secured together (e.g., with glue, molding techniques, etc.); and (iii) a base unit 100 utilizing a manually cocked pinch valve 15. This manual pinch valve construction can be advantageous in further reducing the size of the pinch valve and hence reducing the size of the base unit 100. In this embodiment of the invention, after fault detection and correction, the system has to be reset manually by compressing the valve's spring-loaded pinch bar until it is cocked in place. Upon the detection of a gas bubble in the sensor loop, the locking mechanism is electronically released.

Figure 25:
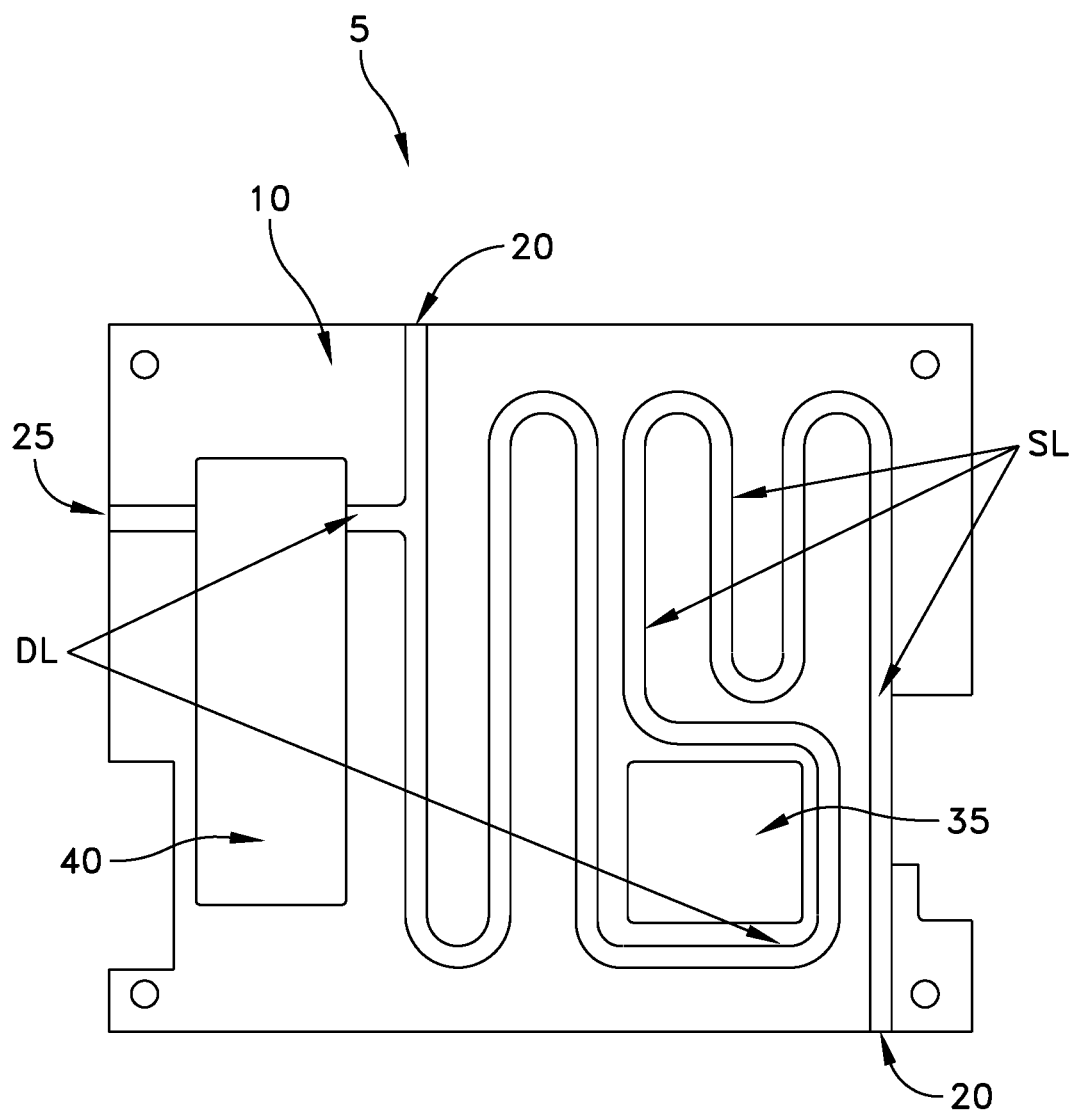
FIG. 25 is a schematic view showing another alternative form of the disposable cassette.
Figure 26:
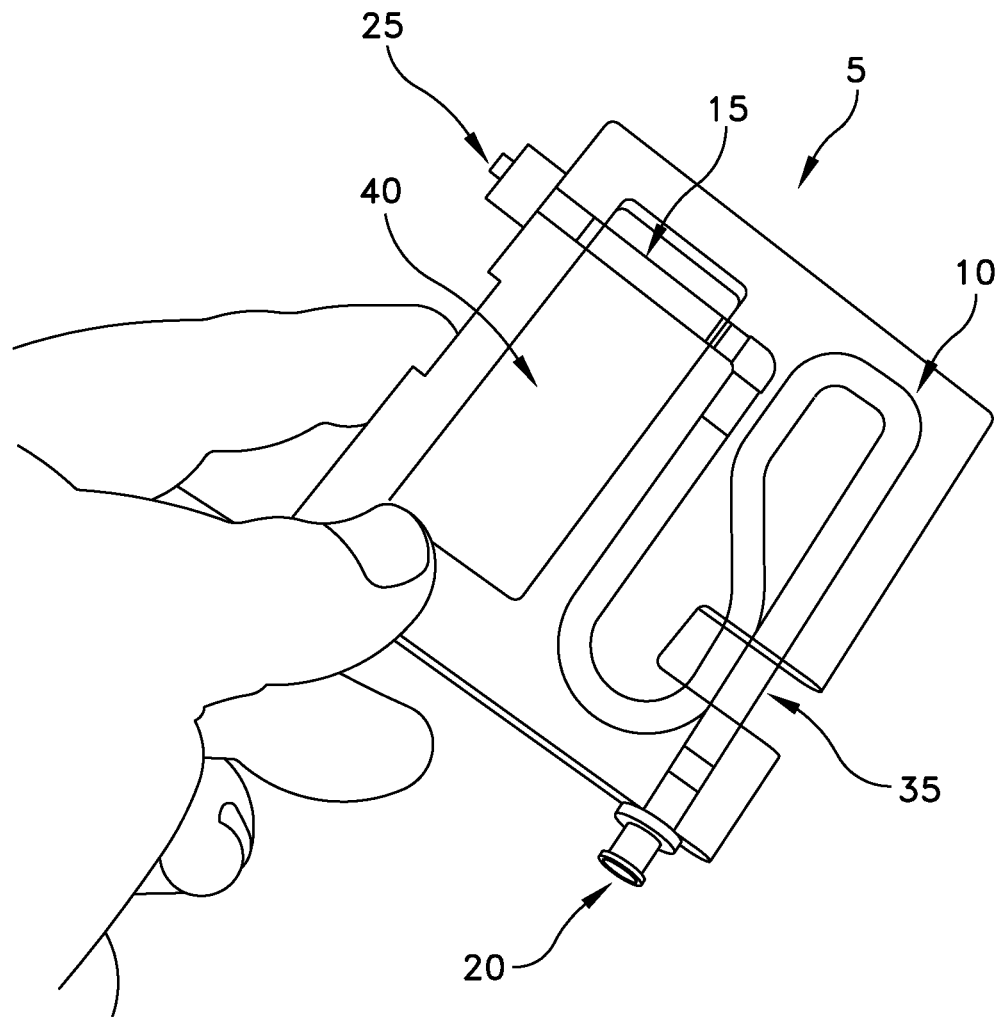
FIGS. 26-34 are various schematic views showing another preferred embodiment of the new system for detecting a gas bubble in a fluid line, entrapping the gas bubble, and purging the gas bubble before the gas bubble can enter the patient's vascular system.
Figure 27:
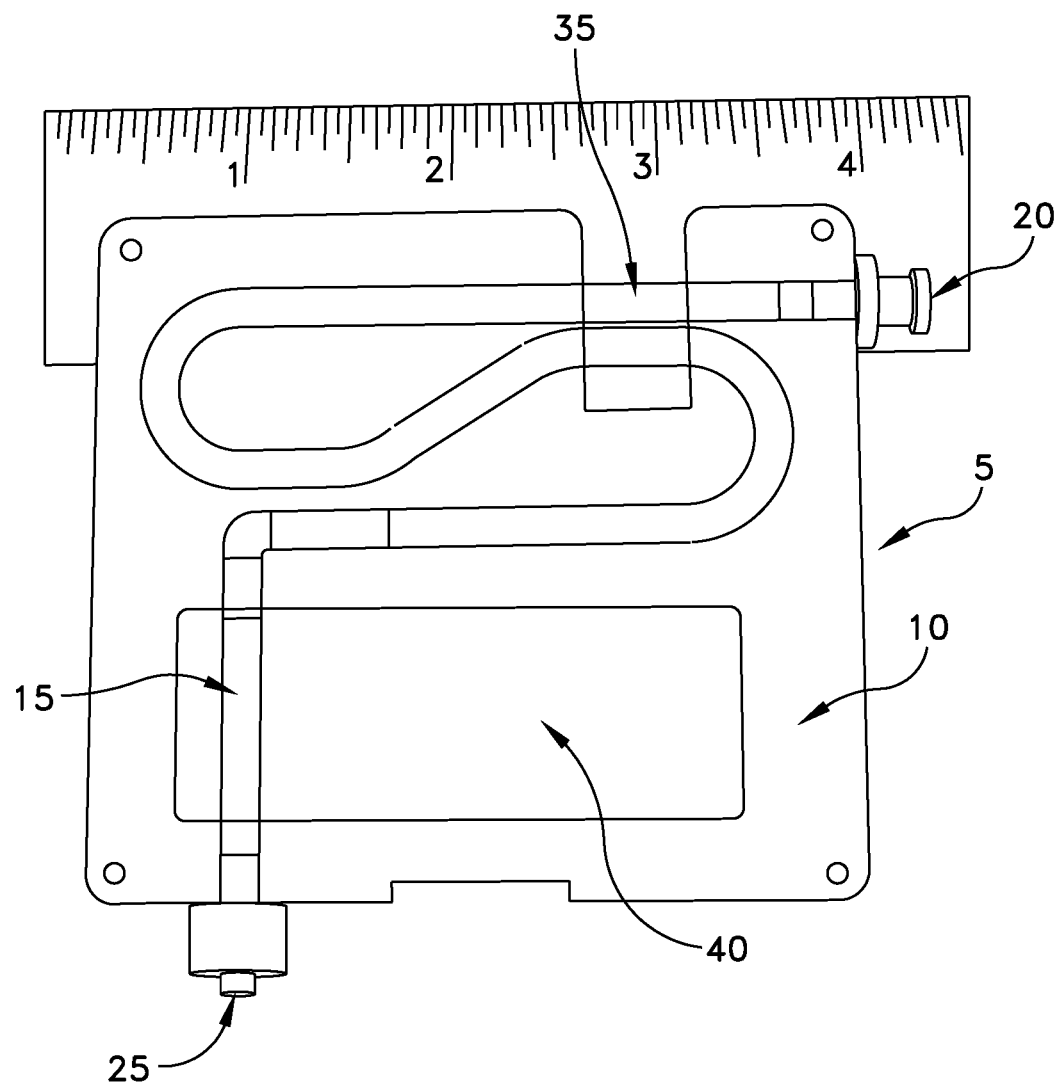
Figure 28:
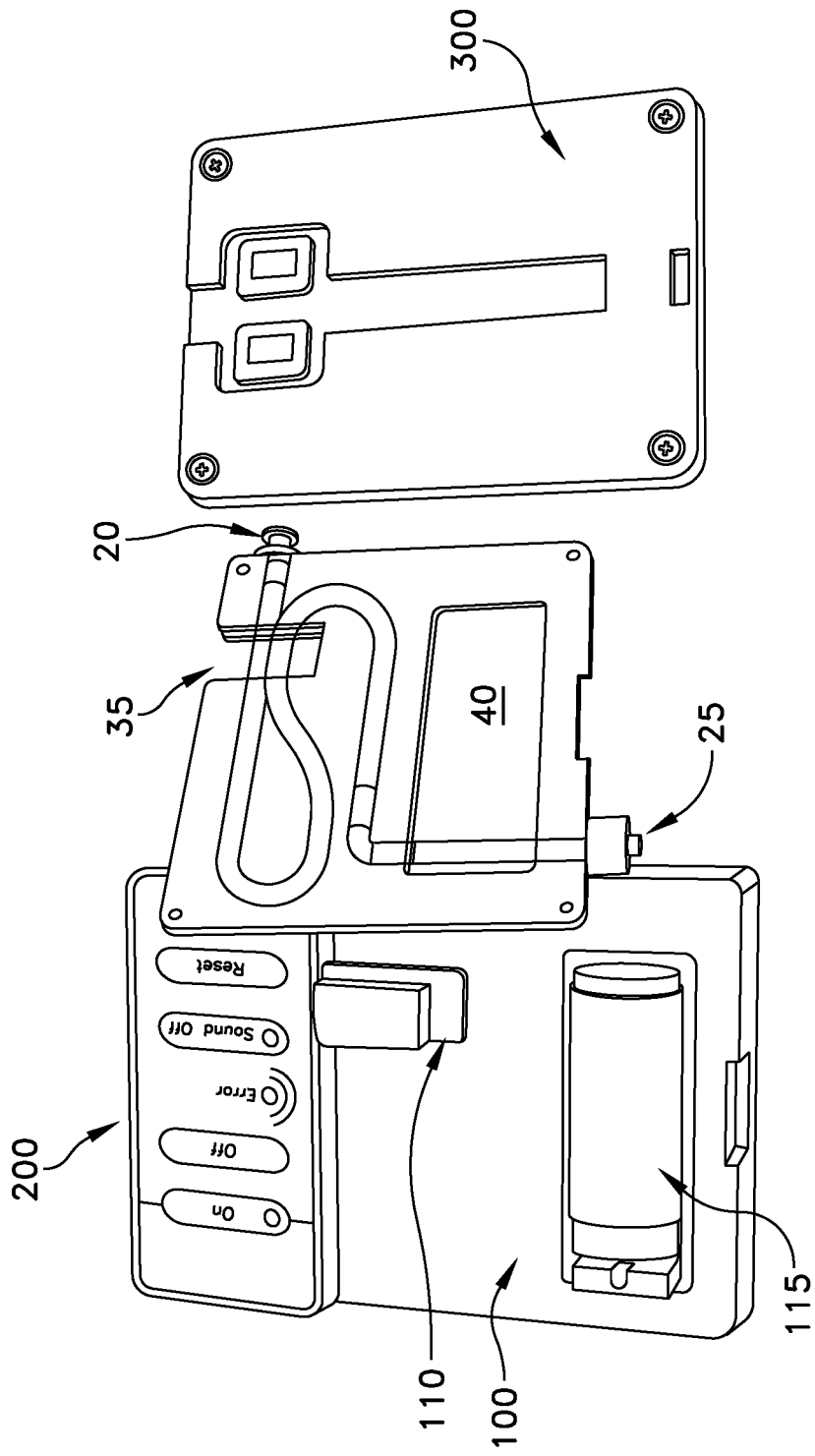
Figure 29:
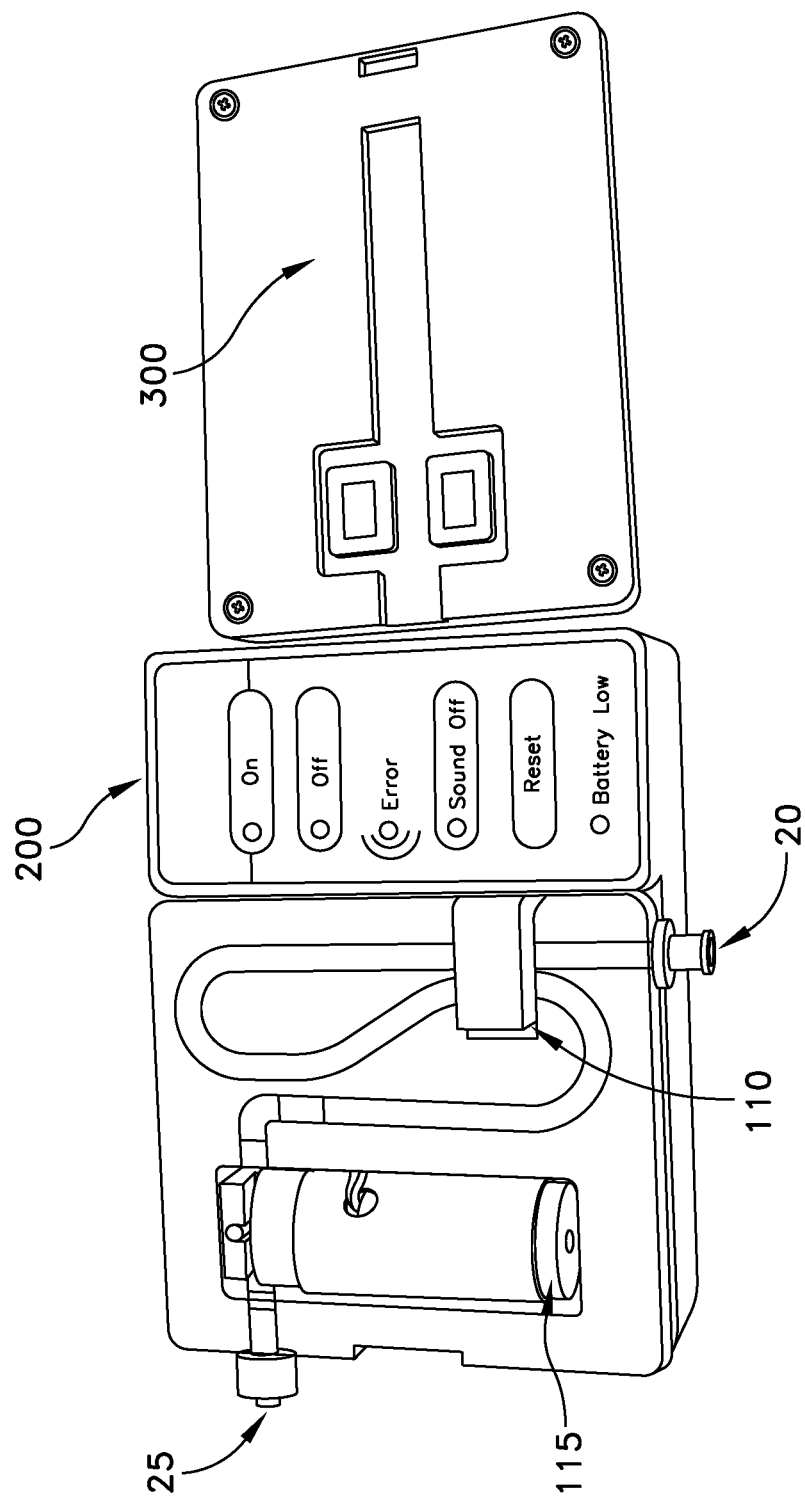
Figure 30:
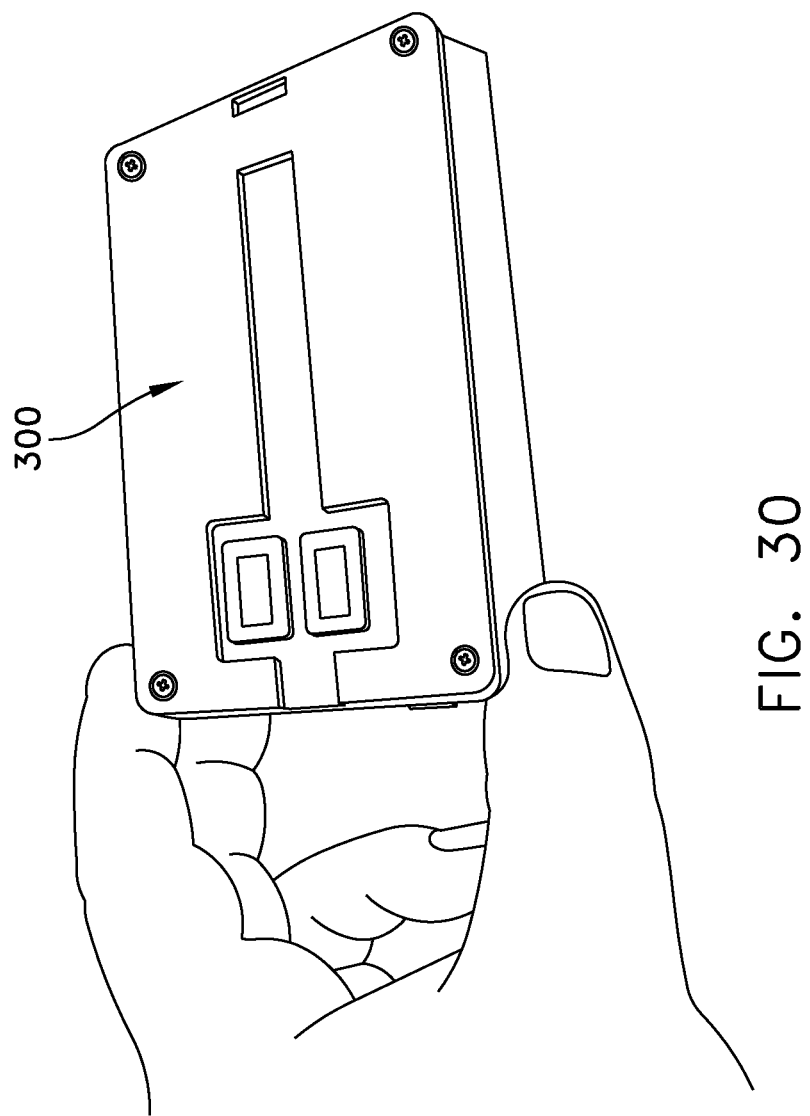
Figure 31:
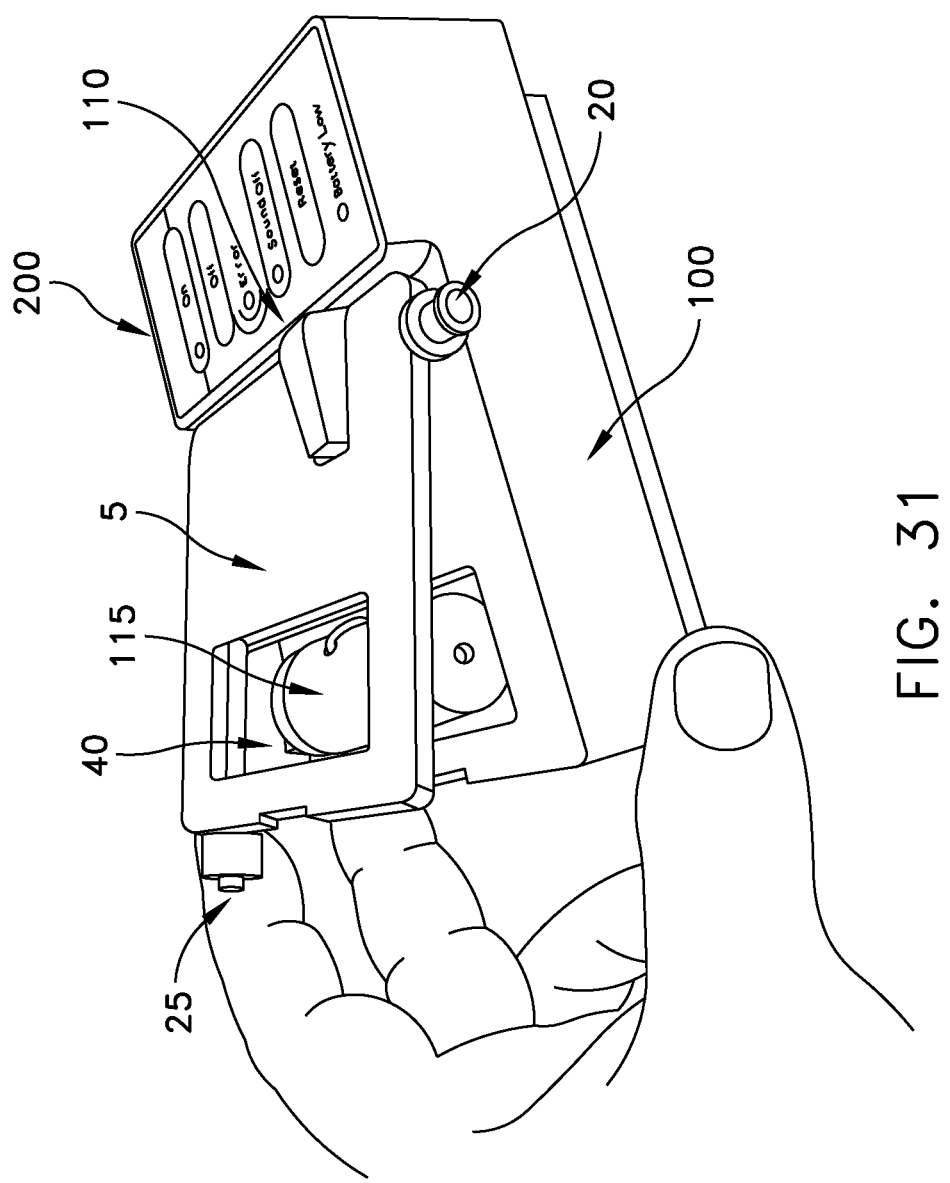
Figure 32:
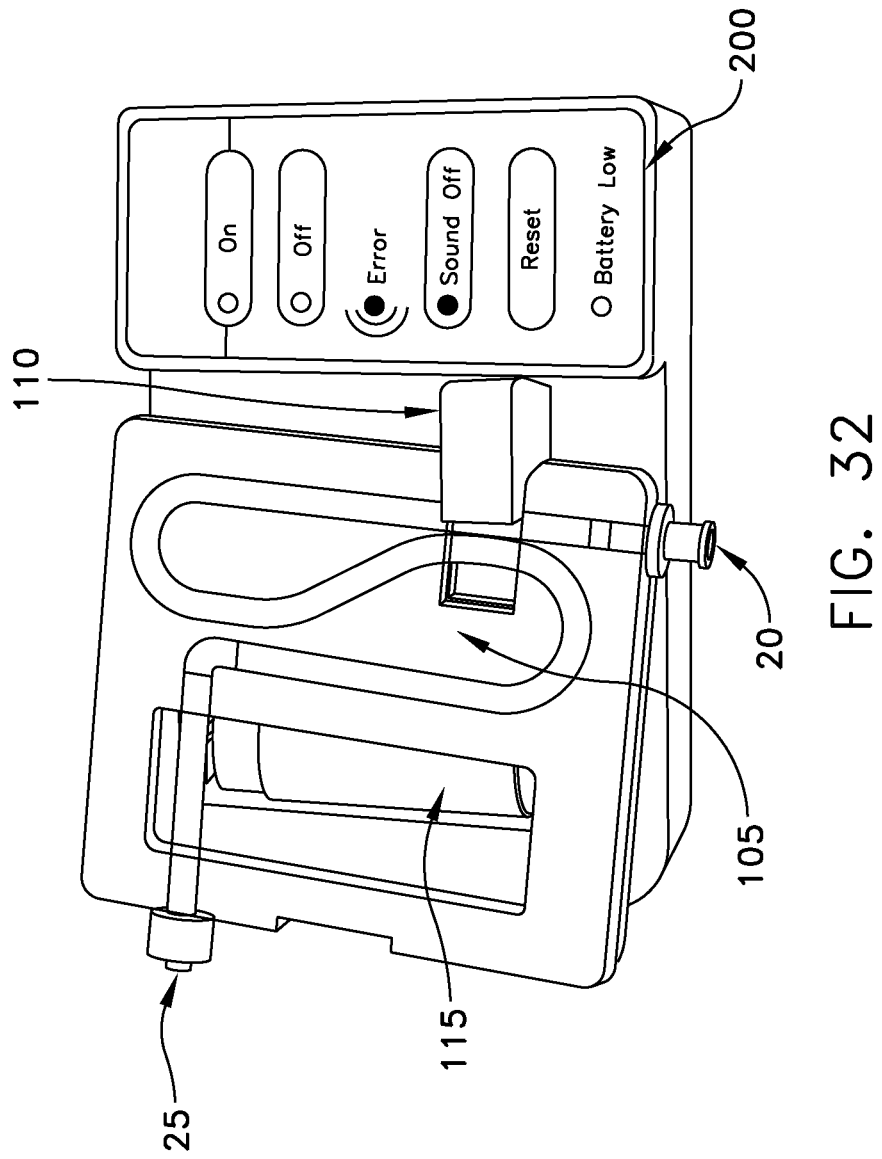
Figure 33:
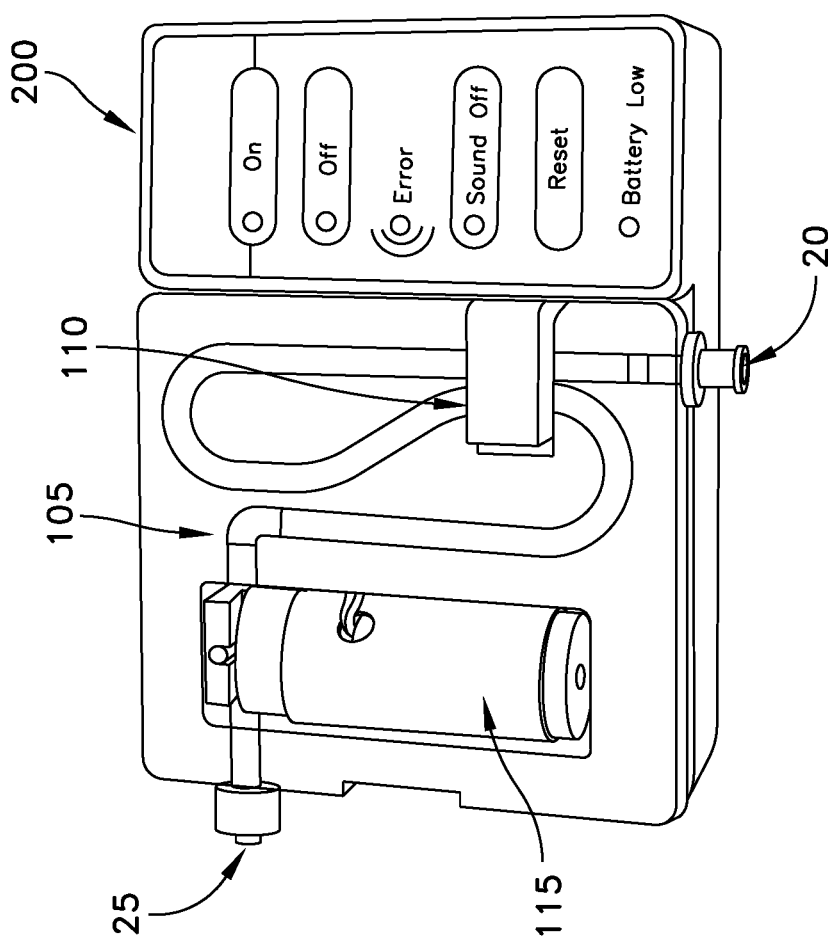
Figure 34:
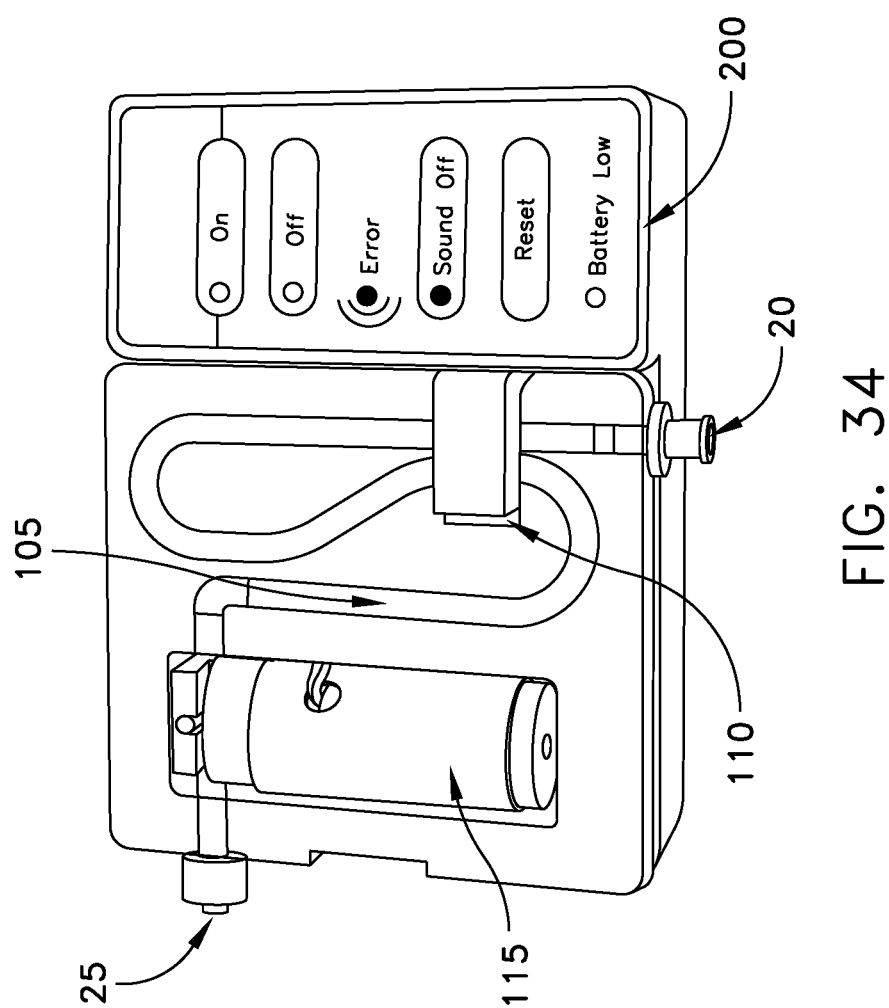

Looking next at FIG. 25, it will be seen that the geometry of the disposable cassette's tubing 15 can be arranged as desired so as to provide the desired sensor loop SL and delay loop DL.

Looking next at FIGS. 26-34, there is shown still another novel system for detecting and removing a gas bubble from a liquid infusion line. In this form of the invention, the base unit 100 and the electronic control unit 200 are contained in the same housing. Also shown is a detachable battery pack 300 for powering the system.

System with Automatic Fluid Diversion

The system described above is adapted to stop fluid flow to the patient upon the detection of a gas bubble, and then requires the operator to intervene by manually bleeding the gas bubble out of the line and then resetting the system.

In an alternative construction, this intervention is automated in the sense that, upon detection of a gas bubble, the flow of liquid (e.g. IV liquid) is diverted to a collection bag until the sensor 110 once again detects liquid in the IV line. When sensor 110 again detects liquid in the IV line, the gas bubble between sensor 110 and the flow diverting mechanism is flushed out of the system before flow is diverted back to the patient. This can be accomplished in various ways. By way of example but not limitation:
  (i) at the onset of a procedure, the operator can set a control on the electronic control unit 200 to reflect the estimated IV flow rate—this flow rate sets a time delay for the diverting mechanism, whereby to delay the diversion of the flow back to the patient after sensor 110 once again detects liquid; or
  (ii) a second gas bubble sensor (not shown) can be positioned in the system, at the diverting mechanism, to control switching the fluid flow back to the patient after sensor 110 and the second gas bubble sensor both detect liquid in the line.

The diverting mechanism can take many different forms. For example, the diverting mechanism can be a disposable Y connector molded into the disposable cartridge 5 and an integral part of the disposable cartridge, with the bottom part of the Y connected to sensor 110, downstream from the liquid delay loop DL of the disposable cartridge 5. The second gas bubble sensor is positioned to detect a gas bubble in the central part of the Y. A two-sided pinch valve 115 is attached to the two top parts of the Y; this pinch valve has two pinching stations, and is arranged so that when one station is open, the other station is closed. A normally open side of pinch valve 115 is positioned at one of the top forks of the Y and the normally closed part of the pinch valve 115 is positioned on the other side of the fork in the top part of the Y. Simple activation of the pinch valve 115 now will allow the flow to be diverted from one side of the disposable cartridge Y to the other. The appropriate side will be connected to the patient; the other side is connected to the collection bag.

A further device configuration would allow for yet a third gas bubble sensor (not shown) to be incorporated in the device. The third gas bubble sensor can be a clamp-on sensor to be positioned on the tubing slightly downstream from the IV bag or other fluid source, to detect when the IV bag is empty, to halt the flow or divert it from the patient and then sound an alarm, signaling an empty IV bag.

In the preceding disclosure, means were disclosed for selectively diverting the flow of fluid away from the patient (when the fluid flow contains a gas bubble) and then an automatic resumption of fluid flow to the patient (when the gas bubble has been purged from the line).

In another form of the invention, the fluid flow, upon detection of a gas bubble, is automatically diverted away from the patient using any of several methods disclosed above or any other suitable means for diverting the gas embolus and maintaining the safety of the patient; but then the fluid flow is not automatically diverted back to the patient but, rather, continues to be directed away from the patient until the attendant resets the device. This will allow the attendant to assess the situation and reset the system when appropriate.

The above embodiments can be incorporated singly or in combination with any of the other system iterations.

An alternate electronic method to trigger the pinch valve 115, or to reroute the fluid flow to a collection bag or back to the patient, entails the electronic calculation of the time the sensor 110 senses a gas bubble in the tubing. By way of example, if a quantity of gas is passing through the sensor 110, an electronic signal signifying "gas" is triggered at the onset of the gas bolus, and the electronic control unit 200 senses the time that the "gas signal" came on. The internal cross-sectional area of the tubing 15 is known. An automatic calculation is performed as to the gas volume passing through the line. If one sensor is used, the gas volume passing through is calculated using an assumed flow rate. This also allows for the calculation of the velocity of the fluid. In turn, this allows for the calculation of the pressure drop in the tubing, allowing for a volume adjustment of the gas flowing through. This calculation is done in real-time and continuously updates its information and, when a predetermined gas volume is sensed, the system triggers its mode of action (e.g., shuts off, alarms, diverts the flow, etc.).

For more precise performance, the use of two sensors in series, positioned a known distance apart, may be utilized. The sensor configuration and positioning should follow the basic parameters of the system, allowing sufficient time for action before releasing the fluid to the patient.

Additional Constructions

Figure 35:
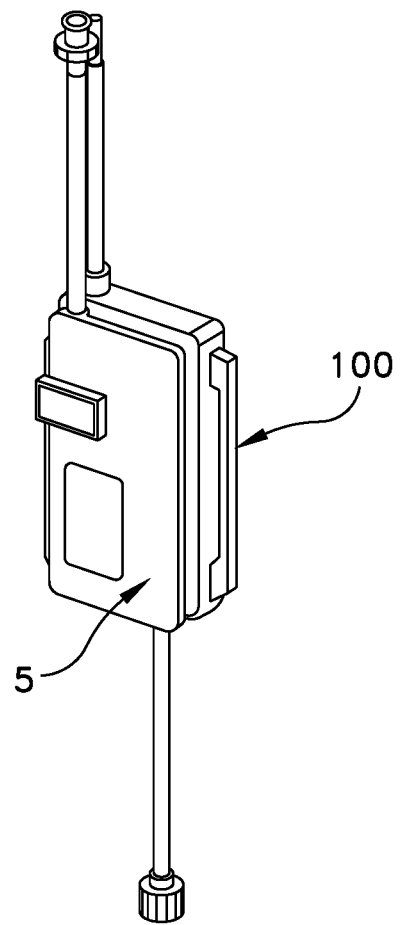
FIG. 35 is a schematic view showing an alternative disposable cassette in conjunction with an alternative base incorporating the sensing unit for remote mounting.
Figure 36:
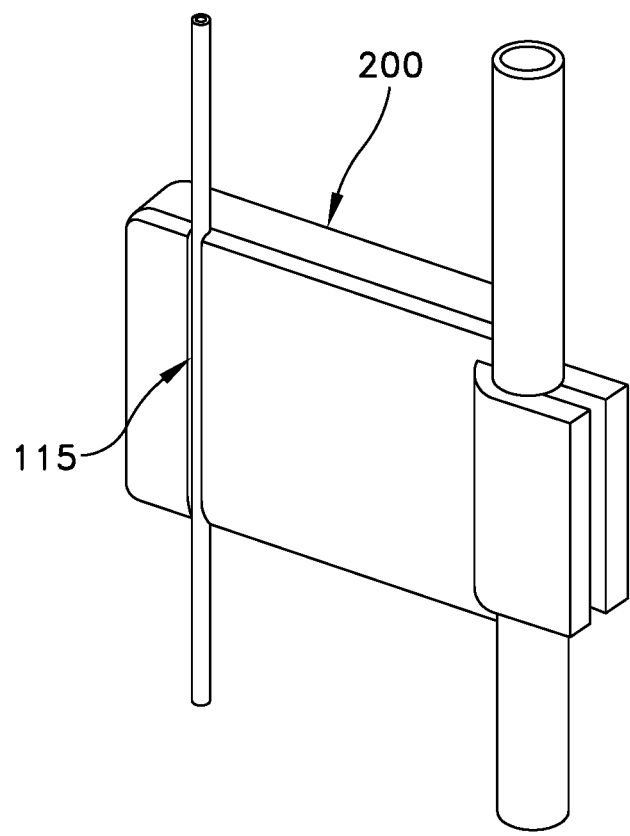
FIG. 36 is a schematic view of an alternative electrical control unit incorporating a pinch valve.
Figure 37:
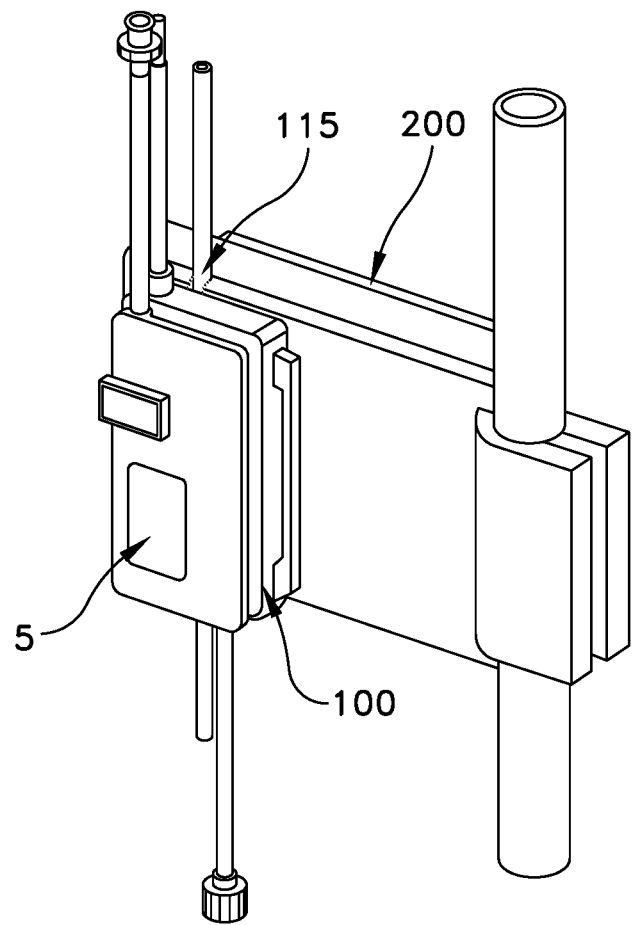
FIG. 37 is a schematic view showing a system configuration where the alternative disposable cassette of FIG. 35, the alternative base unit of FIG. 35, and the alternative electrical control unit of FIG. 36 are all mounted on an IV pole.
Figures 38, 39:
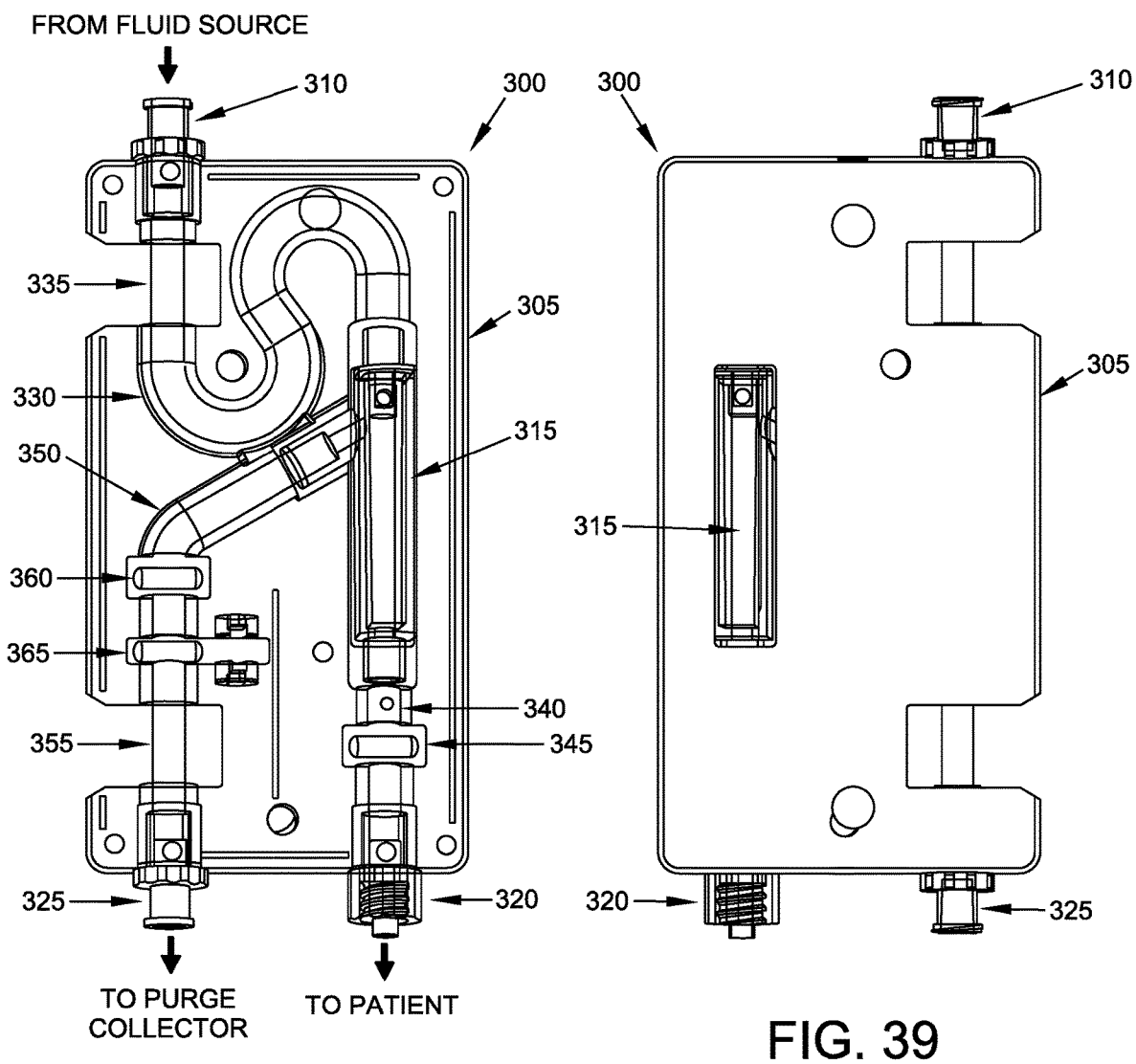
FIGS. 38-41 are schematic views showing another disposable cassette formed in accordance with the present invention, with FIG. 38 being a front view, FIG. 39 being a rear view, FIG. 40 being a front perspective view and FIG. 41 being a rear perspective view.
Figure 40:
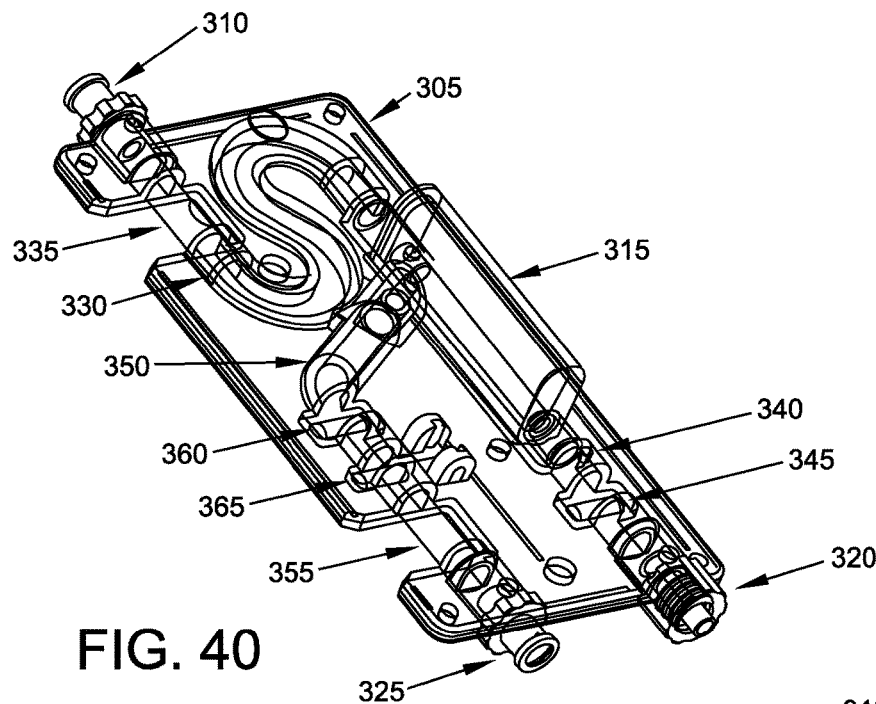
Figure 41:
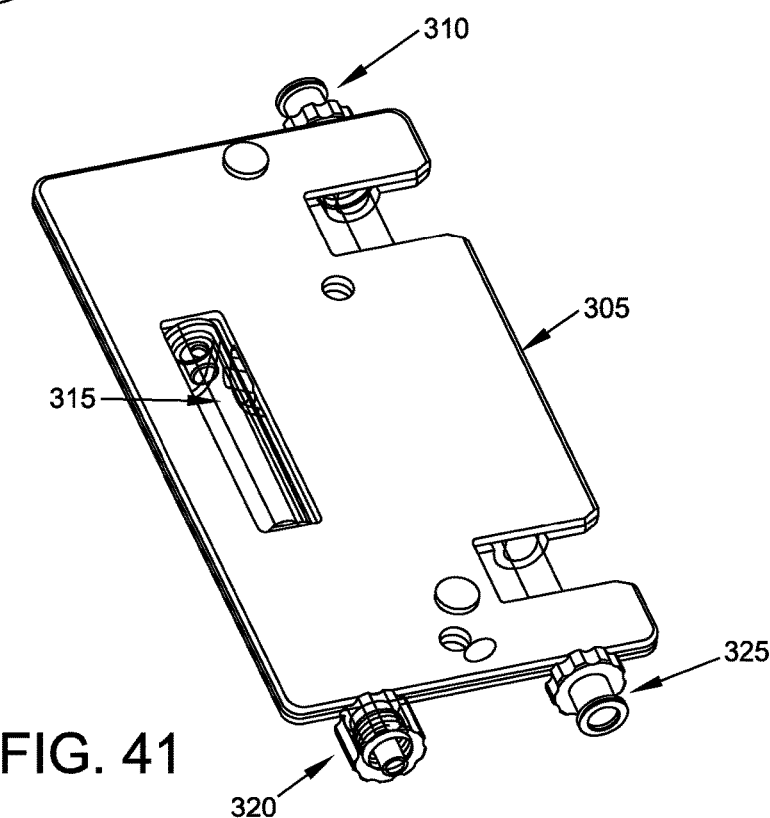

Various modifications can be made to the embodiments disclosed above. By way of example but not limitation:
  (1) the sensor 110 can use IR (infra red) to detect the presence of a gas bubble;
  (2) the sensor 110 can use electrical resistance to detect the presence of a gas bubble;
  (3) the sensor 110 can use sound-based technologies (e.g., Doppler technology) to detect the presence of a gas bubble;

(4) the sensor 110 can comprise a float in the liquid circuit to gate fluid flow: with this arrangement, the float rises in the presence of liquid, opening an outlet port, but the float sinks in the presence of a gas bubble, closing an outlet port—a resistance or a magnetic detector then senses the float position and signals a system fault;

(5) safety devices can be incorporated to automatically indicate correct (or incorrect) engagement of the disposable cassette 5 on base unit 100;

(6) an indicator may be provided to show delivery of an adequate tube-pinching force;

(7) a wireless connection may be provided between base unit 100 and electronic control unit 200—thus, for example, and looking now at FIG. 35, a disposable cassette 5 and base unit 100 may be separated from electronic control unit 200, with the units communicating through a wireless connection; or, if desired, the pinch valve 115 may be located with the electronic control unit 200 (FIG. 36) and/or, if desired, disposable cassette 5, base unit 100 and electronic control unit 200 may all be mounted from an IV pole (FIG. 37);

(8) the sensor station 35 of the disposable cassette 5 (which is positioned adjacent to sensor 110) may be treated with an ultrasound coupling medium such as Vaseline, or a water jell, or whatever is appropriate, so as to ensure a satisfactory coupling to the ultrasound sensor 110—the coating may also contain a solvent and/or an abrasive to clean the sensor 110 and sensor station 35;

(9) as an alternative or in combination with the foregoing, means could be provided to clean the sensor 110 as the disposable cassette 5 is mounted adjacent to the sensor 110—by way of example, this could be accomplished by a mechanical shield covering the disposable tubing 15 which, when removed, will clean the sensor cavity;

(10) cassette 5 need not be disposable—it could be reusable if desired;

(11) cassette 5 could be formed with a passageway, wherein only portions of the passageway comprise flexible tubing—the remainder of the passageway could be formed as a flow path through body 10, or as rigid tubing, etc.;

(12) the construction can be something other than flexible tubing and a pinch valve to selectively close off fluid flow—by way of example but not limitation, cassette 5 could include a traditional flow valve, and base unit 100 could include a mechanism (e.g., a solenoid) for opening that flow control valve; and

(13) if desired, the purge port can be omitted.

Additional Cassette Construction

In another form of the invention, and looking now at FIGS. 38-41, there is provided a disposable cassette 300. Disposable cassette 300 is adapted for disposition intermediate a fluid line (e.g., an IV line), whereby fluid flowing through the disposable cassette may be monitored and, if a gas bubble (e.g., an air bubble) is detected within the fluid flow, the fluid flow may be stopped and the gas bubble removed from the fluid flow before continuing the fluid flow to the patient. Disposable cassette 300 generally comprises a body 305 comprising an inlet port 310, a chamber 315, an outlet port 320, and a purge port 325.

A first passageway 330 connects inlet port 310 to chamber 315. First passageway 330 comprises a bubble detection section 335 where a gas bubble may be detected within first passageway 330.

A second passageway 340 connects chamber 315 with outlet port 320. A pinch valve 345 is disposed along second passageway 340 intermediate chamber 315 and outlet port 320, such that pinch valve 345 can selectively close off second passageway 340 to fluid flow.

A third passageway 350 connects chamber 315 with purge port 325. In one preferred form of the invention, third passageway 350 connects with the uppermost portion of chamber 315, such that no air can accumulate in chamber 315. Third passageway 350 comprises a bubble detection section 355 where a gas bubble may be detected within third passageway 350. A pinch valve 360 is disposed along third passageway 350 intermediate chamber 315 and bubble detection section 355, such that pinch valve 360 can selectively close off third passageway 350.

If desired, another pinch valve 365 may be disposed along third passageway 350 intermediate pinch valve 360 and bubble detection section 355, such that pinch valve 365 can selectively close off third passageway 350.

Figure 42:
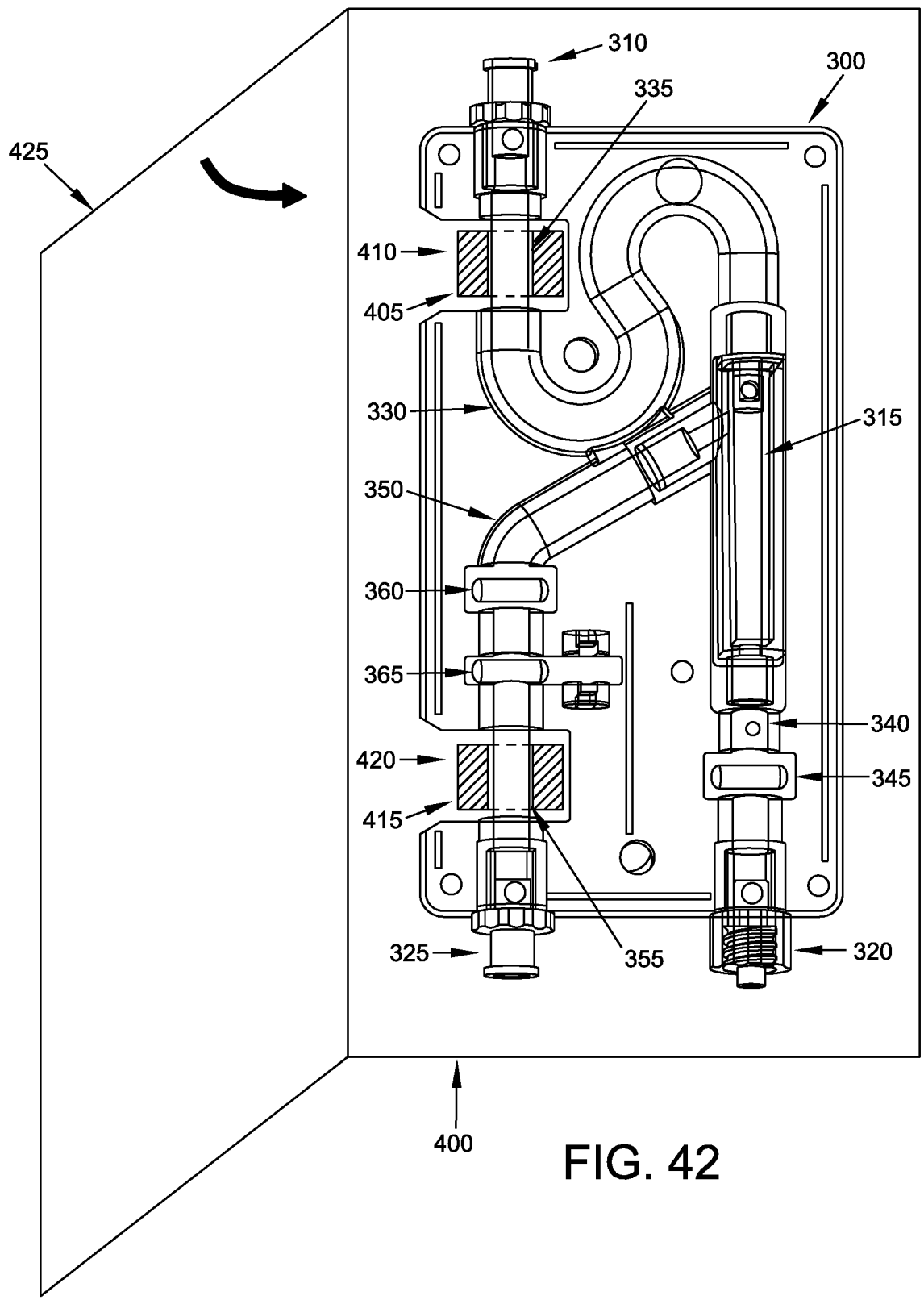
FIG. 42 is a schematic view showing the disposable cassette of FIGS. 38-41 mounted to a base unit.
Figure 43:
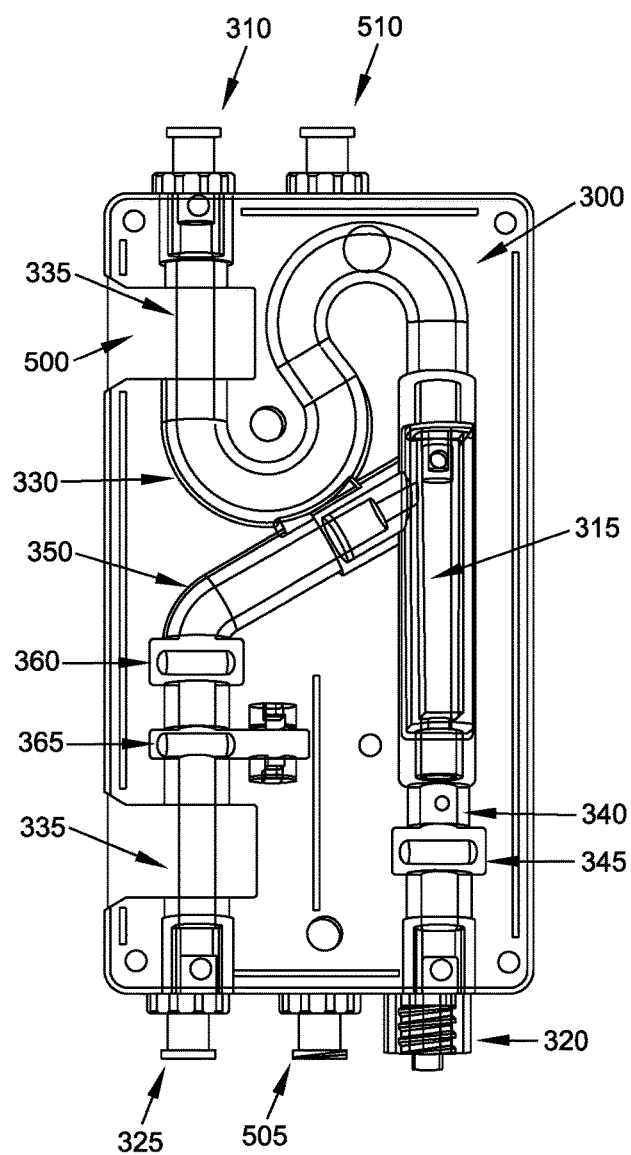
FIGS. 43-46 are schematic views showing a fluid warmer mounted to the disposable cassette of FIGS. 38-41, with FIG. 43 being a front view, FIG. 44 being a rear view, FIG. 45 being a front perspective view and FIG. 46 being a rear perspective view.
Figure 44:
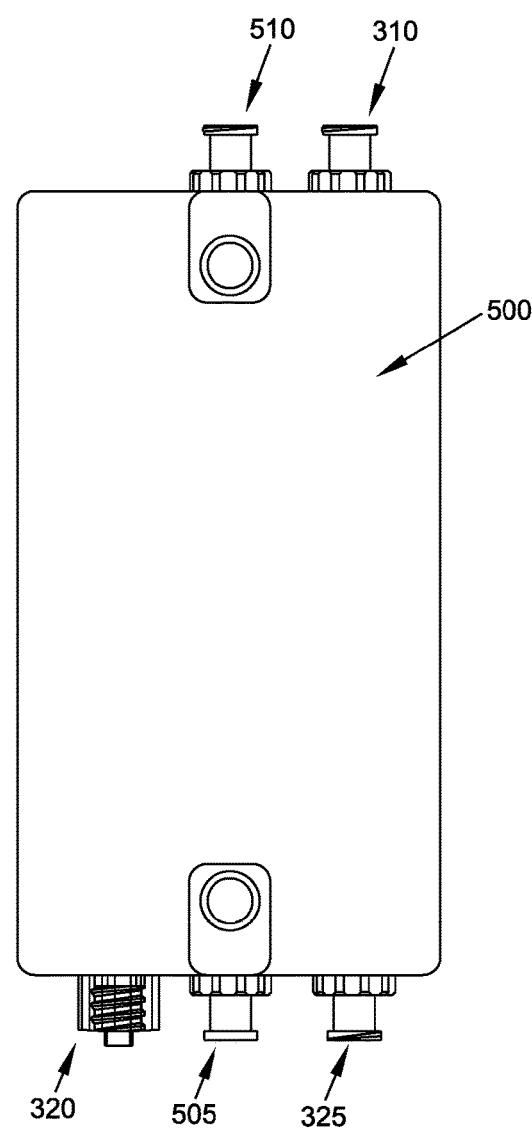
Figure 45:
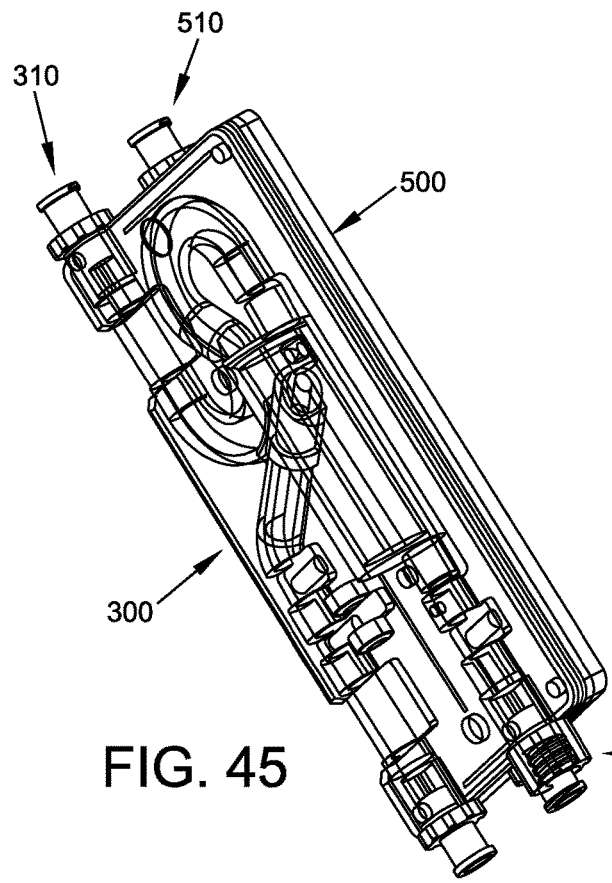
Figure 46:
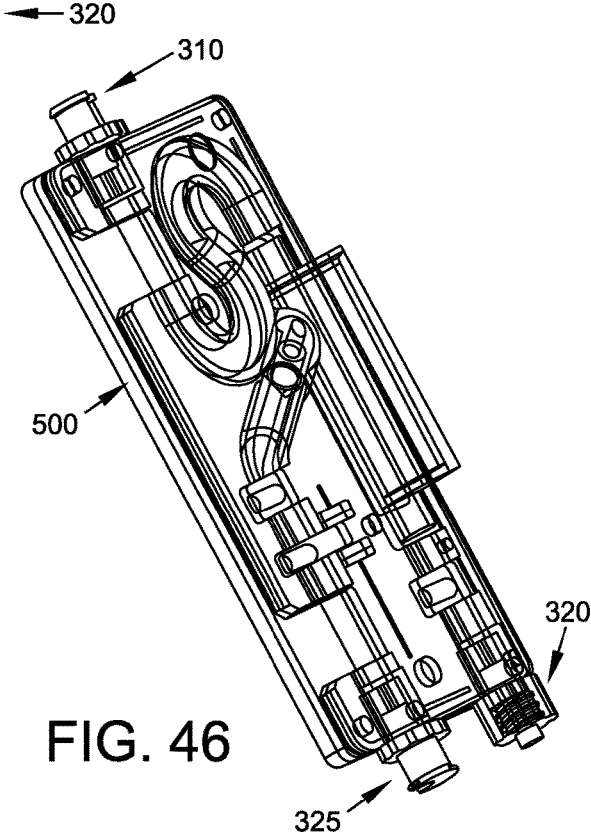
Figure 47:
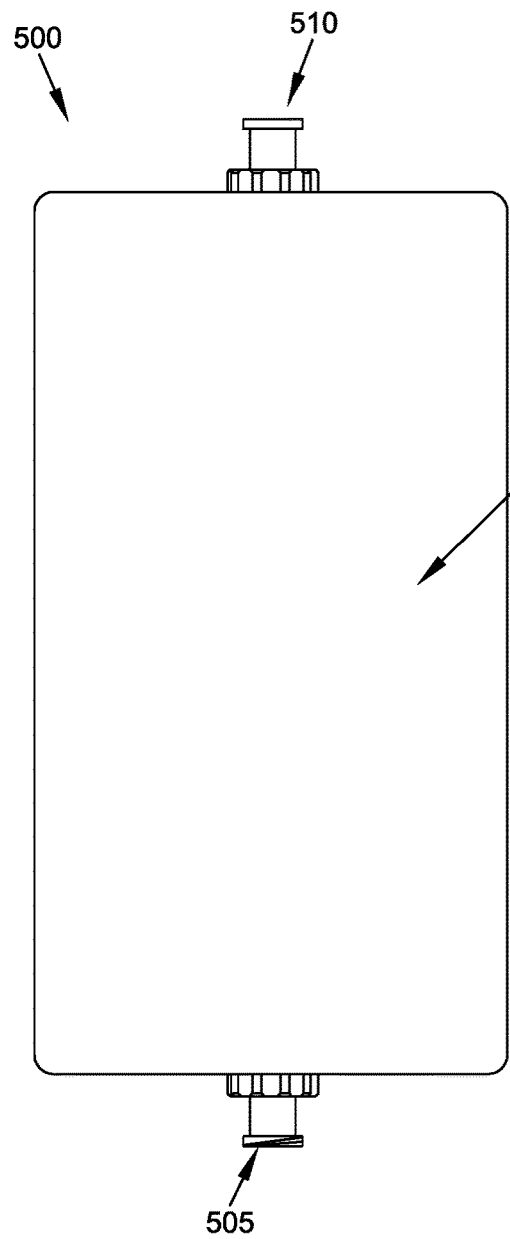
FIGS. 47-52 are schematic views showing the fluid warmer of FIGS. 43-46, with FIG. 47 being a front view, FIG. 48 being a rear view, FIG. 49 being a front perspective view, FIG. 50 being a rear perspective view, and with FIGS. 51 and 52 showing various components of the fluid warmer.
Figure 48:
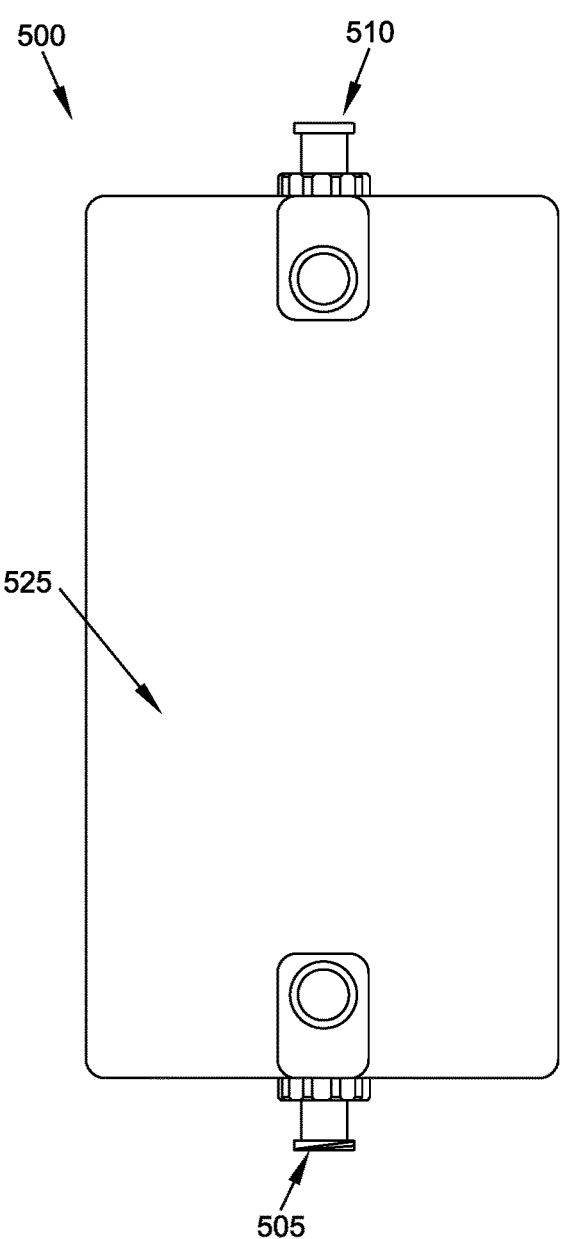
Figure 49:
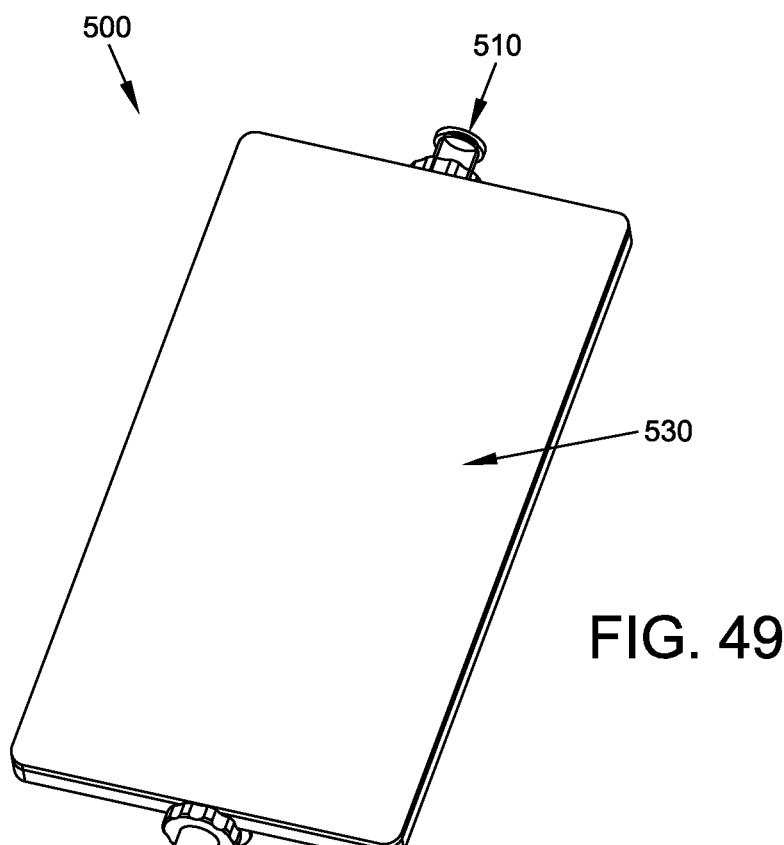
Figure 50:
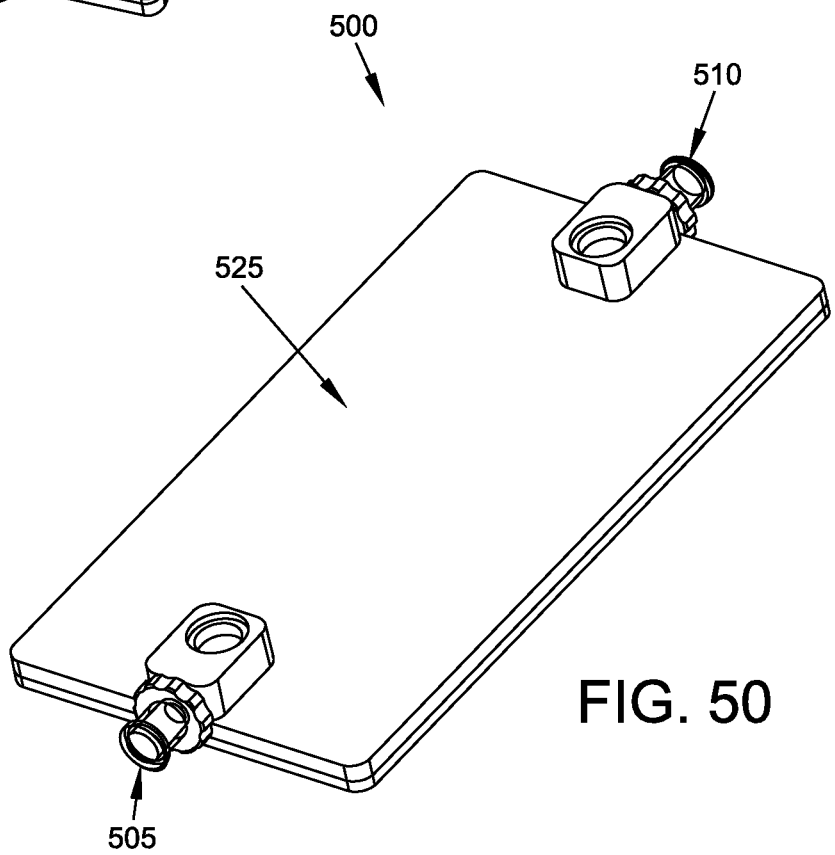
Figure 51:
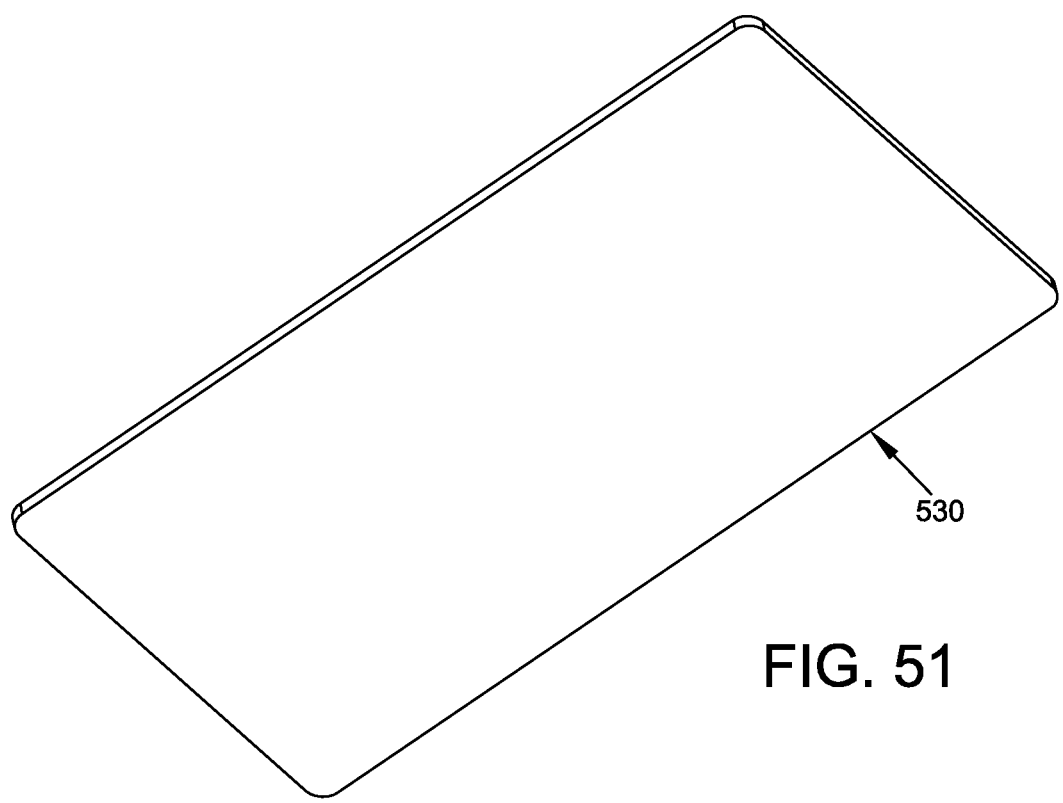
Figure 52:
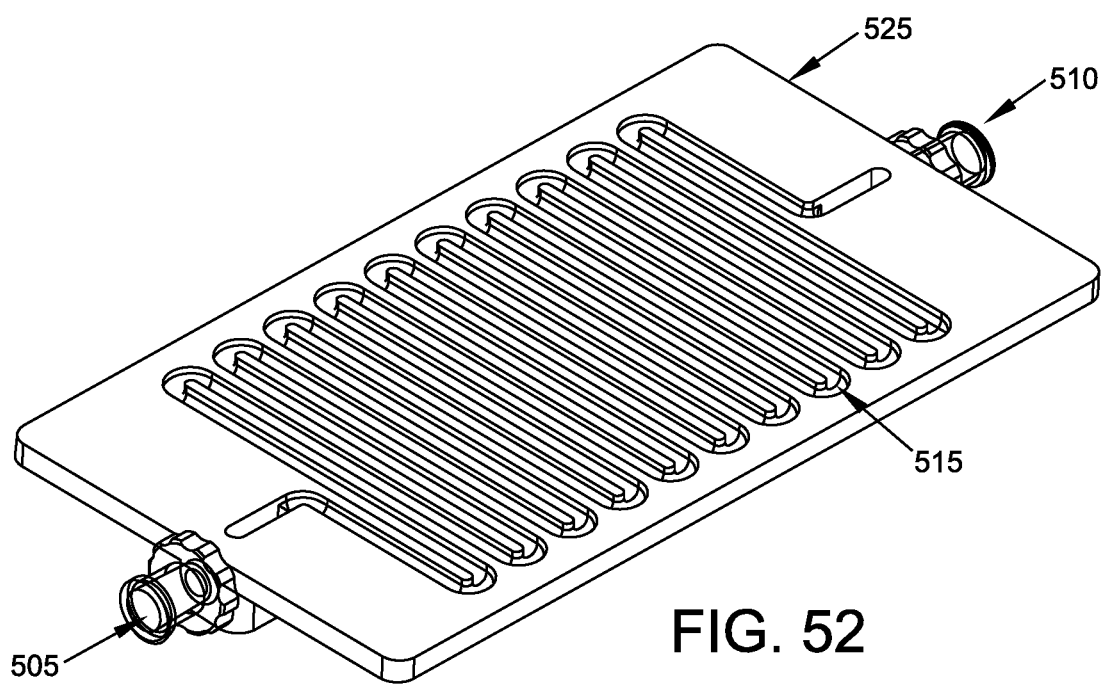
Figure 53:
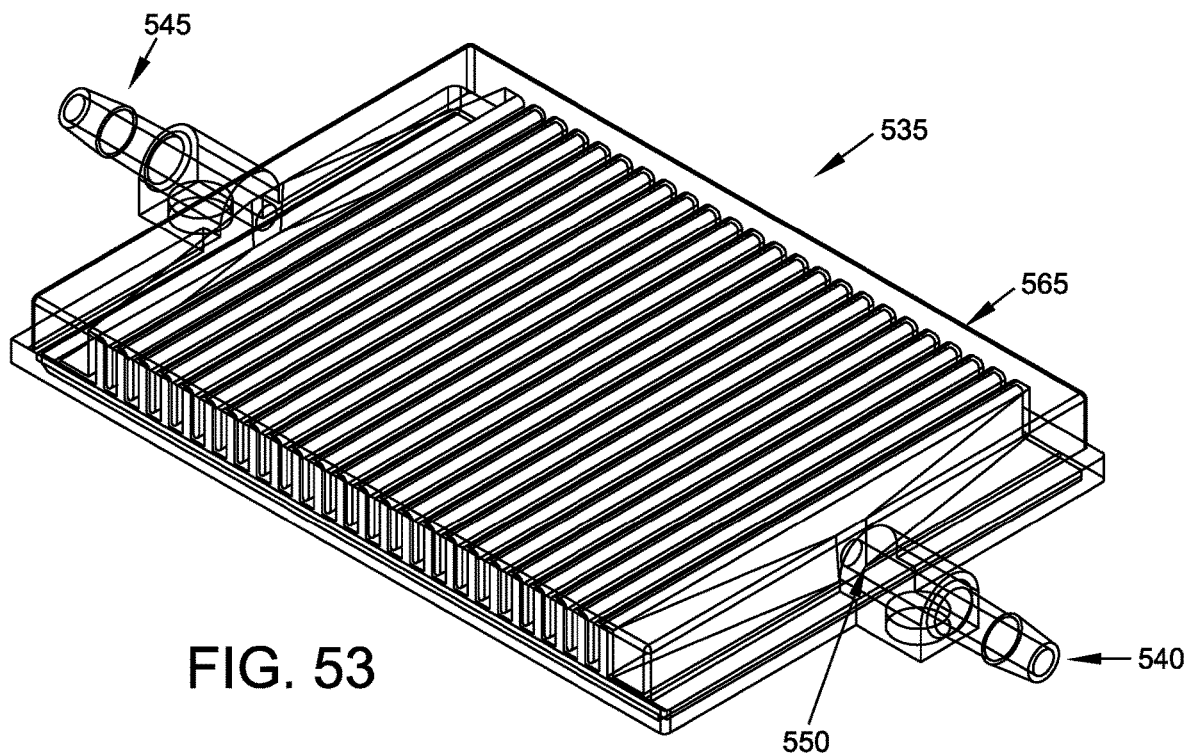
FIGS. 53-56 are schematic views showing an alternative form of the fluid warmer, with FIG. 53 being a front perspective view, FIG. 54 being a front perspective view of one of the components of the fluid warmer, FIG. 55 being a front perspective sectional view of one of the components of the fluid warmer and FIG. 56 being a side sectional view of one of the components of the fluid warmer.
Figure 54:
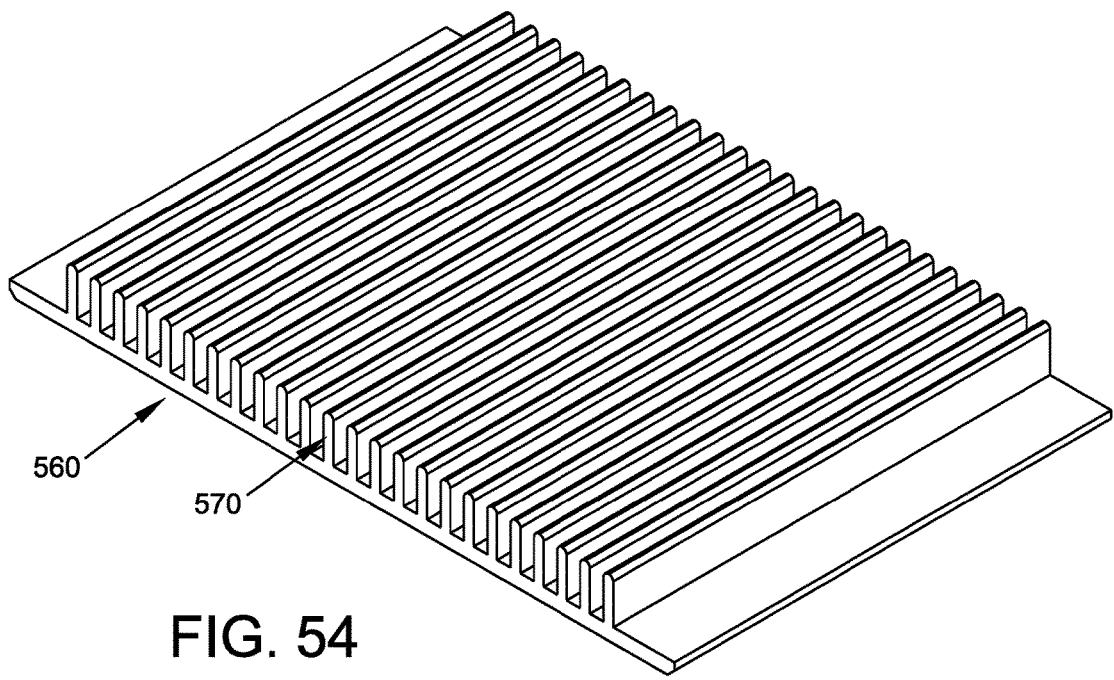
Figure 55:
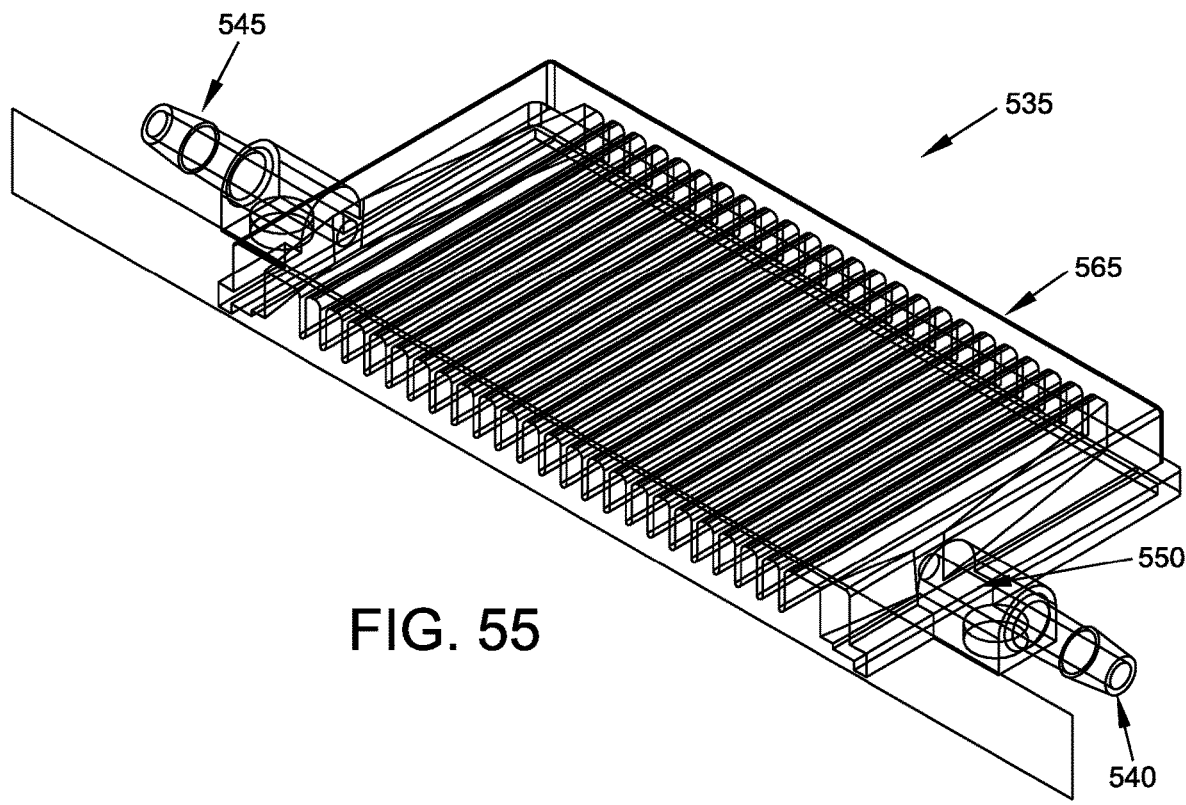
Figure 56:
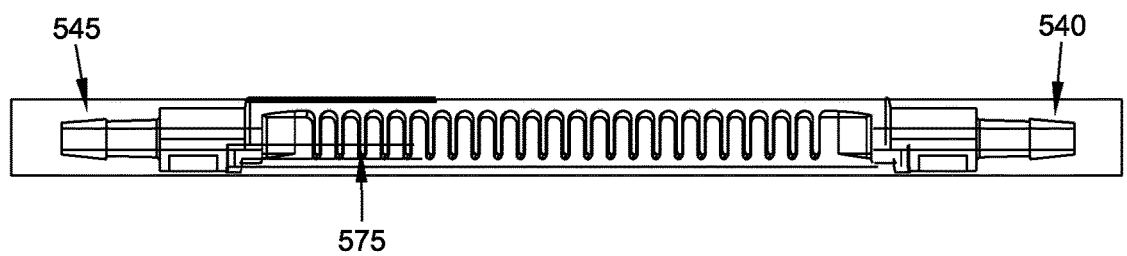

In use, and looking now at FIG. 42, a disposable cassette 300 is withdrawn from its sterilized package and loaded into a base unit, e.g., a base unit 400 having a sensor 405 at a sensor station 410 for detecting the presence of a gas bubble at bubble detection section 335 of first passageway 330, and a sensor 415 at a sensor station 420 for detecting the presence of a gas bubble at bubble detection section 355 of third passageway 350. Pinch valve 345 in second passageway 340 is set to its open position, and pinch valve 360 in third passageway 350 is set to its closed position. If a pinch valve 365 is provided in third passageway 350, pinch valve 365 is set to its open position.

Then the "source side" of a fluid line (e.g., an IV line) is connected to the disposable cassette's inlet port 310, the disposable cassette's outlet port 320 is connected to the "patient side" of the fluid line, and the purge port 325 is connected to a purge collector (e.g., a collection bag, etc.).

The fluid line is then primed, air removed, etc., so that the fluid line is ready to infuse the patient.

Next, fluid is allowed to flow from the fluid source, into inlet port 310, through first passageway 330, into chamber 315, past pinch valve 345, out outlet port 320, and to the patient. As the fluid flows through disposable cassette 300, sensor 405 at sensor station 410 monitors the fluid flow, sensing for the presence of a gas bubble. So long as no gas bubble is detected, the fluid is allowed to flow uninterrupted, thereby infusing the patient with the desired fluid.

In the event that sensor 405 at sensor station 410 detects the presence of a gas bubble (e.g., an air bubble) in the fluid, base unit 400 closes off pinch valve 345 in second passageway 340, thereby closing off flow to the patient, and opens pinch valve 360 in third passageway 350, thereby allowing fluid to flow from chamber 315, through third passageway 350 and out purge port 325 to the purge collector (e.g., a collection bag). As the fluid flow flows through third passageway 350, sensor 415 at sensor station 420 monitors the fluid flow sensing for the presence of a gas bubble. So long as a gas bubble is detected, the fluid is allowed to flow out purge port 325. However, when a gas bubble is no longer detected in the fluid flow, base unit 400 closes off pinch valve 360 in third passageway 350, terminating fluid flow out purge port 325, and opens pinch valve 345 in second passageway 340, thereby restoring fluid flow to the patient.

In this way, disposable cassette 300 may serve to ensure that gas bubbles in the fluid flow are prevented from being introduced into the patient.

As noted above, a pinch valve 365 may be disposed along third passageway 350 intermediate pinch valve 360 and bubble detection section 355. This pinch valve may be set so that it is normally in an open position, but automatically closes upon the occurrence of an event, e.g., the opening of a front door 425 on base unit 400.

Fluid Warmer

In another form of the present invention, and looking now at FIGS. 43-46, a fluid warmer 500 may be provided, preferably for use adjacent to disposable cassette 300. Such a fluid warmer can be desirable, inasmuch as a fluid being introduced into the patient may be relatively cold (e.g., such as if the fluid were stored in a refrigerator) and can produce discomfort for the patient if the fluid is introduced at a cold temperature. In addition, it has been found that as a fluid warms, gases entrained in the fluid may be released, causing bubbling in the fluid. To the extent that this occurs, it is preferable that this bubbling occurs upstream of the patient (and preferably upstream of disposable cassette 300), rather than once the fluid has been introduced into the patient. To that end, fluid warmer 500 provides a means for warming the fluid prior to its introduction into the patient.

In one preferred form of the invention, and looking now at FIGS. 47-52, fluid warmer 500 comprises an inlet port 505, an outlet port 510 and a passageway 515 extending therebetween. Passageway 515 is preferably serpentine, so as to increase the dwell time of the fluid passing through the fluid warmer, whereby to allow heat content to be introduced into the fluid. Fluid passing through fluid warmer 500 is heated as the fluid passes through passageway 515 in fluid warmer 500, e.g., by a heater (not shown) which is disposed in base unit 400 adjacent to fluid warmer 500. In one preferred form of the invention, fluid warmer 500 comprises (i) a base 525 comprising inlet port 505, outlet port 510, and passageway 515, wherein passageway 515 is a serpentine surface groove formed in base 525, and (ii) a plate 530 for closing off the serpentine surface groove (whereby to provide a fluid-tight passageway 515).

In one preferred form of the invention, passageway 515 may have surface texturing which can facilitate the release of entrained gases from the fluid. Again, fluid warmer 500 is preferably disposed upstream of disposable cassette 300, so that the disposable cassette 300 can remove gas bubbles prior to introduction to the patient.

In one preferred form of the invention, and as seen in FIGS. 43-46, fluid warmer 500 has a form factor similar to disposable cassette 300, such that fluid warmer 500 can conveniently abut disposable cassette 300 when positioned in a base unit, e.g., base unit 400. In one preferred form of the invention, the inlet port 505 of fluid warmer 500 is connected to the fluid source, and the outlet port 510 of fluid warmer 500 is connected to inlet port 310 of disposable cassette 300. As a result, any gases that may be released from the fluid as the fluid warms in fluid warmer 500 will be released upstream of disposable cassette 300, thereby providing the disposable cassette with the opportunity to purge the gases before they are introduced into the patient.

In another preferred form of the invention, and looking now at FIGS. 53-56, there is provided a fluid warmer 535 which comprises an inlet port 540, an outlet port 545 and a passageway 550 extending therebetween. Passageway 550 preferably comprises a corrugated configuration, so as to increase the dwell time of the fluid passing through the fluid warmer. Fluid passing through fluid warmer 535 is heated as the fluid passes through passageway 550 in fluid warmer 535, e.g., by a heater (not shown) which is disposed in base unit 400 adjacent to fluid warmer 535. In one preferred form of the invention, fluid warmer 535 comprises a base 560 and a cover 565. Base 560 comprises a plurality of baffle plates 570 for defining one half of passageway 550. Cover 565 comprises inlet port 540, outlet port 545 and a plurality of baffle plates 575 for defining the other half of passageway 550. It will be appreciated that when base 560 and cover 565 are assembled together, their respective baffle plates 570, 575, intersperse so as to form a corrugated structure over which the fluid flows as it passes through fluid warmer 535.

Collapsible Chamber to Prevent Entrapment of Air

In fluid lines, it is frequently desirable to provide a drip chamber intermediate the fluid line, distal to the fluid source and proximal to the patient. Typically, this drip chamber has air in it. However, if the chamber should inadvertently be tipped (e.g., such as if an IV pole should be accidentally knocked over), air from the drip chamber may inadvertently enter the fluid line and thereafter pass into the patient which, as noted above, can have serious consequences.

Figure 57:
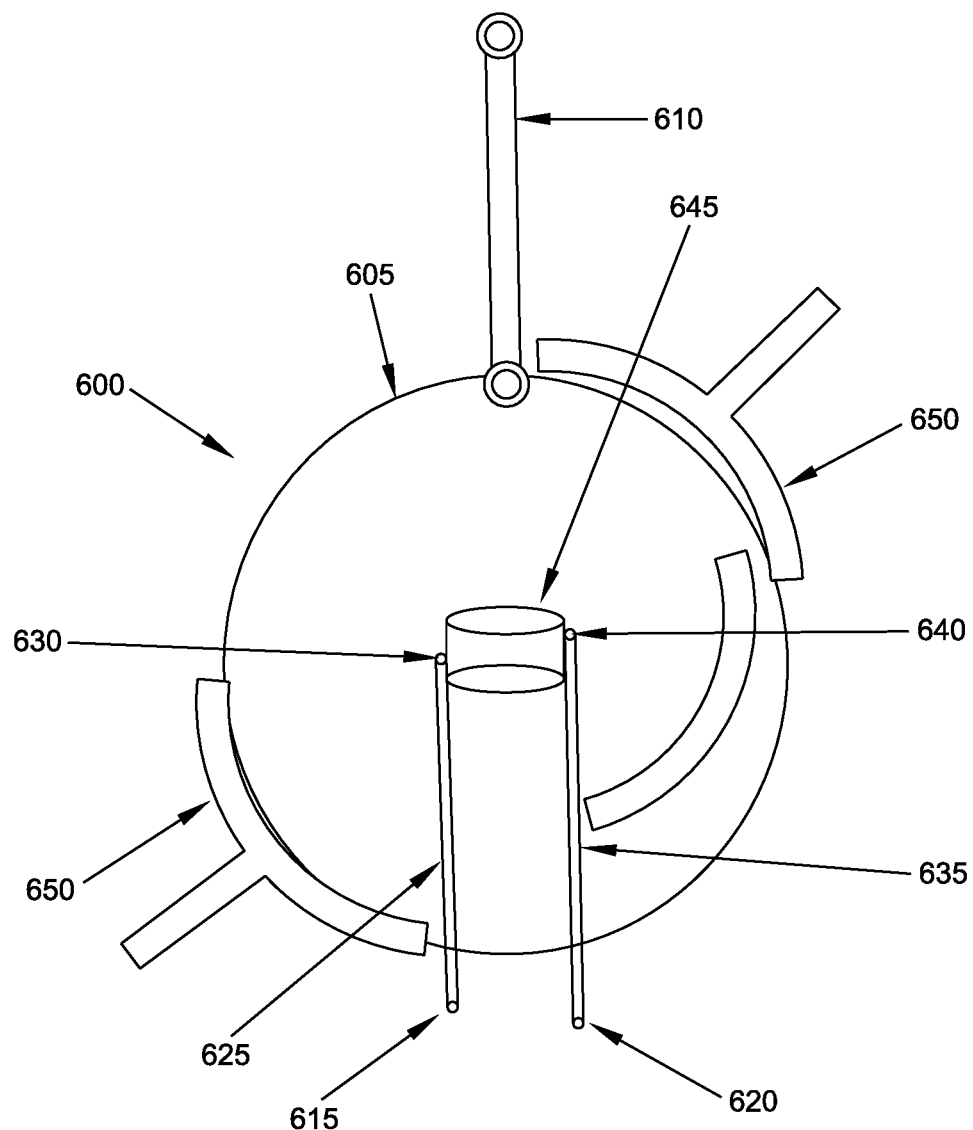
FIG. 57 is a schematic view showing a collapsible chamber formed in accordance with the present invention.

To this end, and looking now at FIG. 57, there is provided a collapsible chamber 600 which can ensure that air from the drip chamber does not enter the fluid which is passed to the patient. More particularly, in this form of the invention, collapsible chamber 600 comprises a bladder 605 having an inlet port 610 for connection to a fluid source, an outlet port 615 for connection to the patient, and a purge port 620 for connection to a purge collector (e.g., a collection bag, etc.). In this form of the invention, outlet port 615 comprises a flexible tube 625 which terminates in a mouth 630, and purge port 620 comprises a flexible tube 635 which terminates in a mouth 640. Collapsible chamber 600 also comprises a float 645. Flexible tube 625 is secured to float 645 so that mouth 630 of outlet port 615 is disposed below the float, and flexible tube 635 is secured to float 645 so that mouth 640 of purge port 620 is disposed above the float.

As a result of this construction, when a combination of air and fluid is disposed in bladder 605, mouth 630 of outlet port 615 is disposed in the fluid and mouth 640 of purge port 620 is disposed in the air, so that fluid is transferred to the patient and air is transferred to the purge port. However, if the level of fluid in bladder 605 should fall too low, float 645 falls back on, and covers, mouth 630 of outlet port 615, whereby to prevent air from being introduced into the patient. At this point, mouth 640 of purge port 620 can be used to bleed air from bladder 605, whereby to reestablish an appropriate level of fluid in the bladder.

If desired, one or more compression devices 650 may be provided to compress bladder 605, whereby to accelerate the removal of air from bladder 605.

Figure 58:
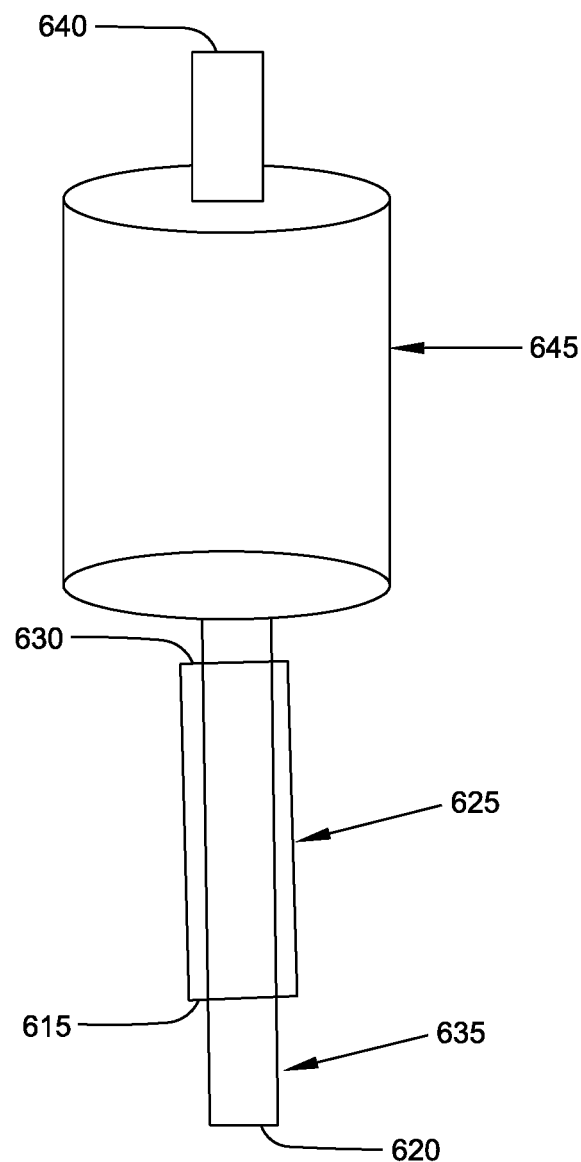
FIG. 58 is a schematic view showing an alternative construction for a portion of the collapsible chamber shown in FIG. 57.

FIG. 58 shows an alternative construction, wherein tubes 625 and 635 are relatively rigid and concentric with one another, with tube 635 telescoping from tube 625, and with float 645 secured to tube 635. In this form of the invention, when there is adequate fluid in bladder 605, float 645 is spaced from mouth 630 of outlet port 615, so that fluid is transferred to the patient. However, when the level of fluid in bladder 605 falls too low, float 645 falls back on, and covers, mouth 630 of outlet port 615, such that no air is transferred to the patient.

Figure 59:
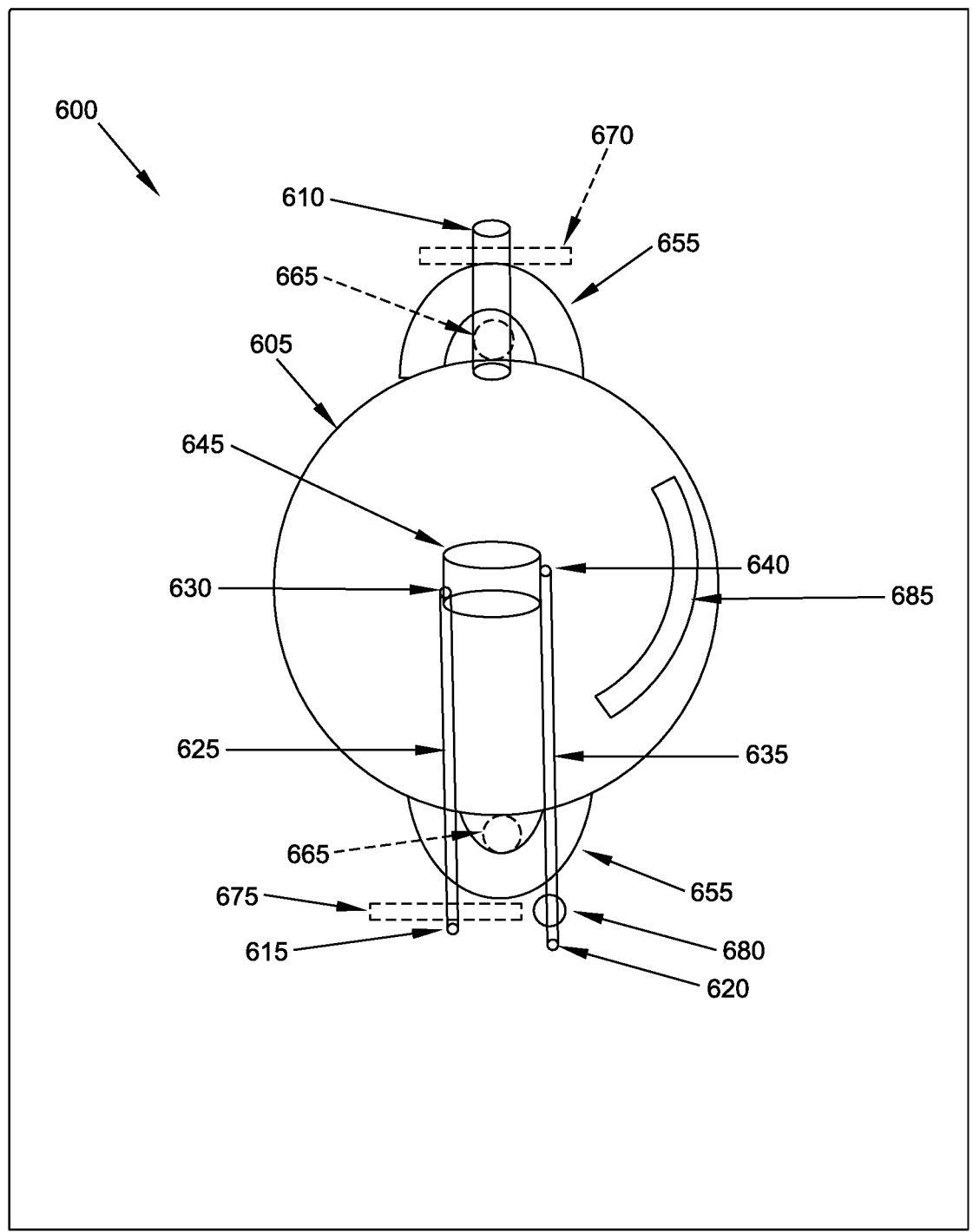
FIG. 59 is a schematic view showing another collapsible chamber formed in accordance with the present invention.

FIG. 59 shows a construction which is generally similar to the construction shown in FIG. 57. More particularly, in this form of the invention, collapsible chamber 600 comprises a bladder 605 having an inlet port 610 for connection to a fluid source, an outlet port 615 for connection to the patient, and a purge port 620 for connection to a purge collector (e.g., a collection bag, etc.) or open to the atmosphere through a bacterial filter. In this form of the invention, outlet port 615 comprises a flexible tube 625 which terminates in a mouth 630, and purge port 620 comprises a flexible tube 635 which terminates in a mouth 640. Collapsible chamber 600 also comprises a float 645. Flexible tube 625 is secured to float 645 so that mouth 630 of outlet port 615 is disposed below the float, and flexible tube 635 is secured to float 645 so that mouth 640 of purge port 620 is disposed above the float. In addition, in this form of the invention, bladder 605 include mounts 655 for mounting collapsible chamber 600 to a support structure, e.g., a support structure 660 which includes a pair of pins 665 which are movable towards or away from one another, with mounts 655 being mounted to pins 665. In this way, support structure 660 can be used to compress bladder 605 in a controlled fashion (i.e., by moving pins 665 toward one another) or expand bladder 605 in a controlled fashion (i.e., by moving pins 665 away from one another). In addition, in this form of the invention, inlet port 610 preferably comprises a pinch valve 670, outlet port 615 preferably comprises a pinch valve 675, and purge port 620 preferably comprises a check valve 680.

With this form of the invention, support structure 660 can be used to quickly expel air from bladder 605 through purge port 620, by causing pins 665 to move towards one another (whereby to compress the bladder) while pinch valve 670 in inlet port 610 and the pinch valve 675 in outlet port 615 are simultaneously closed. Support structure 660 can also be used to quickly fill bladder 605 through inlet port 610, by causing pins 665 to move away from one another (whereby to expand the bladder) while pinch valve 670 in inlet port 610 is open and pinch valve 675 in outlet port 615 is closed, whereby to create suction in bladder 605 to fill the cavity to its original level. As this occurs, check valve 680 in purge port 620 will prevent air from flowing back into the bladder from the purge collector (e.g., a collection bag, etc.).

Thus it will be seen that when the level of fluid in collapsible chamber 600 becomes low, such that there is a concern that flow to the patient may be interrupted, support structure 660 can be used to quickly replenish the level of fluid in collapsible chamber 600, i.e., by first compressing bladder 605 (by moving pins 665 toward one another) so as to remove air from bladder 605, and then expanding bladder 605 (by moving pins 665 away from one another) so as to draw fluid into bladder 605.

Preferably collapsible chamber 600 includes a sensor 685 for determining the fluid level within collapsible chamber 600, whereby to determine when bladder compression/expansion should be triggered so as to replenish the fluid contained in bladder 605.

In addition to the foregoing, if lines 625 and 635 are constructed so as to be very flexible and unkinkable, and they are assembled concentrically into float 645, then the position of the collapsible chamber 600 (i.e., vertical or horizontal) will not matter, since the orientation of lines 625 and 635 will be fixed to float 645 and the particular disposition (i.e., orientation) of the collapsible chamber will not affect the function of collapsible chamber 600.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A collapsible chamber for preventing the entrapment of air in a fluid introduced into a patient, the collapsible chamber comprising:
   a collapsible bladder having an inlet port for connection to a fluid source, an outlet port for connection to a patient, and a purge port for connection to a purge collector;
   at least one compression device for selectively compressing the collapsible bladder, whereby to selectively reduce the volume of the collapsible bladder;
   an outlet port tube connected to the outlet port of the collapsible bladder and terminating in an outlet port mouth located within the collapsible bladder;
   a purge port tube connected to the purge port of the collapsible bladder and terminating in a purge port mouth located within the collapsible bladder; and
   a float disposed within the collapsible bladder, the float being movably connected to the outlet port tube and fixedly connected to the purge port tube such that (i) when an appropriate level of fluid is present in the collapsible bladder, the outlet port mouth is connected to the fluid and the purge port mouth is disposed above the fluid, and (ii) when an appropriate level of fluid is not present in the collapsible bladder, the float moves relative to the outlet port mouth so as to seal the outlet port mouth.

2. A collapsible chamber according to claim 1 wherein the outlet port tube and the purge port tube are arranged concentrically.

3. A method for removing a gas bubble from a vascular infusion line, the method comprising:
   providing a collapsible chamber for preventing the entrapment of air in a fluid introduced into a patient, the collapsible chamber comprising:
      a collapsible bladder having an inlet port for connection to a fluid source, an outlet port for connection to a patient, and a purge port for connection to a purge collector;
      at least one compression device for selectively compressing the collapsible bladder, whereby to selectively reduce the volume of the collapsible bladder;
      an outlet port tube connected to the outlet port of the collapsible bladder and terminating in an outlet port mouth located within the collapsible bladder;
      a purge port tube connected to the purge port of the collapsible bladder and terminating in a purge port mouth located within the collapsible bladder; and
      a float disposed within the collapsible bladder, the float being movably connected to the outlet port tube and fixedly connected to the purge port tube such that (i) when an appropriate level of fluid is present in the collapsible bladder, the outlet port mouth is connected to the fluid and the purge port mouth is disposed above the fluid, and (ii) when an appropriate level of fluid is not present in the collapsible bladder, the float moves relative to the outlet port mouth so as to seal the outlet port mouth;
   connecting a fluid source to the inlet port of the collapsible chamber, and connecting the outlet port of the collapsible chamber; and
   using the at least one compression device to compress the collapsible bladder so as to reduce the volume of the collapsible bladder.

4. A collapsible chamber according to claim 1 wherein the outlet port tube and the purge port tube are connected to the float such that the outlet port tube and the purge port tube move when the float moves.

5. A collapsible chamber according to claim 1 wherein the outlet port tube and the purge port tube are connected to the float such that the purge port mouth is disposed higher than the outlet port mouth.

6. A collapsible chamber according to claim 1 wherein the outlet port tube and the purge port tube are flexible and unkinkable, such that when the orientation of the collapsible bladder changes, the outlet port tube and the purge port tube bend as necessary so that the float continues to float on top of the fluid disposed within the collapsible bladder, with the outlet port tube and the purge port tube extending away from the float and into the fluid contained within the collapsible bladder.

7. A method according to claim 3 wherein the outlet port tube and the purge port tube are connected to the float such that the outlet port tube and the purge port tube move when the float moves.

8. A method according to claim 3 wherein the outlet port tube and the purge port tube are connected to the float such that the purge port mouth is disposed higher than the outlet port mouth.

9. A method according to claim 3 wherein the outlet port tube and the purge port tube are flexible and unkinkable, such that when the orientation of the collapsible bladder changes, the outlet port tube and the purge port tube bend as necessary so that the float continues to float on top of the fluid disposed within the collapsible bladder, with the outlet port tube and the purge port tube extending away from the float and into the fluid contained within the collapsible bladder.

10. A collapsible chamber for preventing the entrapment of air in a fluid introduced into a patient, the collapsible chamber comprising:
   a bladder having an inlet port for connection to a fluid source, an outlet port for connection to a patient, and a purge port for connection to a purge collector;
   an outlet port tube connected to the outlet port and terminating in an outlet port mouth;
   a purge port tube connected to the purge port and terminating in a purge port mouth; and
   a float disposed within the bladder, the float being movably connected to the outlet port tube and fixedly connected to the purge port tube such that (i) when an appropriate level of fluid is present in the bladder, the outlet port mouth is connected to the fluid and the purge port mouth is disposed above the fluid, and (ii) when an appropriate level of fluid is not present in the bladder, the float moves relative to the outlet port mouth so as to seal the outlet port mouth;
   wherein the outlet port tube and the purge port tube are flexible and unkinkable, such that when the orientation of the bladder changes, the outlet port tube and the purge port tube bend as necessary so that the float continues to float on top of the fluid disposed in the bladder, with the outlet port tube and the purge port tube extending away from the float and into the fluid contained within the bladder.

11. A collapsible chamber according to claim 10 wherein the outlet port tube and the purge port tube are connected to the float such that the outlet port tube and the purge port tube move when the float moves.

12. A collapsible chamber according to claim 10 wherein the outlet port tube and the purge port tube are connected to the float such that the purge port mouth is disposed higher than the outlet port mouth.

13. A collapsible chamber according to claim 10 wherein the bladder comprises a collapsible bladder, and further wherein the collapsible chamber comprises at least one compression device for selectively compressing the collapsible bladder, whereby to selectively reduce the volume of the collapsible bladder.

14. A method for removing a gas bubble from a vascular infusion line, the method comprising:
   providing a collapsible chamber for preventing the entrapment of air in a fluid introduced into a patient, the collapsible chamber comprising:
      a bladder having an inlet port for connection to a fluid source, an outlet port for connection to a patient, and a purge port for connection to a purge collector;
      an outlet port tube connected to the outlet port and terminating in an outlet port mouth;
      a purge port tube connected to the purge port and terminating in a purge port mouth; and
      a float disposed within the bladder, the float being movably connected to the outlet port tube and fixedly connected to the purge port tube such that (i) when an appropriate level of fluid is present in the bladder, the outlet port mouth is connected to the fluid and the purge port mouth is disposed above the fluid, and (ii) when an appropriate level of fluid is not present in the bladder, the float moves relative to the outlet port mouth so as to seal the outlet port mouth;
      wherein the outlet port tube and the purge port tube are flexible and unkinkable, such that when the orientation of the bladder changes, the outlet port tube and the purge port tube bend as necessary so that the float continues to float on top of the fluid disposed in the bladder, with the outlet port tube and the purge port tube extending away from the float and into the fluid contained within the bladder;
   connecting a fluid source to the inlet port of the collapsible chamber, and connecting the outlet port of the collapsible chamber.

15. A method according to claim 14 wherein the outlet port tube and the purge port tube are connected to the float such that the outlet port tube and the purge port tube move when the float moves.

16. A method according to claim 14 wherein the outlet port tube and the purge port tube are connected to the float such that the purge port mouth is disposed higher than the outlet port mouth.

17. A method according to claim 14 wherein the bladder comprises a collapsible bladder, and further wherein the collapsible chamber comprises at least one compression device for selectively compressing the collapsible bladder, whereby to selectively reduce the volume of the collapsible bladder.

* * * * *